United States Patent
DeJohn et al.

(10) Patent No.: US 12,305,230 B2
(45) Date of Patent: *May 20, 2025

(54) ANALYTIC DEVICE

(71) Applicant: Biomeme, Inc., Philadelphia, PA (US)

(72) Inventors: Marc Dominic DeJohn, Philadelphia, PA (US); Jesse Wilson vanWestrienen, Philadelphia, PA (US); Maximilian Maksutovic, Rohnert Park, CA (US)

(73) Assignee: BIOMEME INC., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,671

(22) Filed: Apr. 26, 2023

(65) Prior Publication Data

US 2023/0265495 A1     Aug. 24, 2023

Related U.S. Application Data

(60) Division of application No. 16/571,535, filed on Sep. 16, 2019, now Pat. No. 11,667,963, which is a
(Continued)

(51) Int. Cl.
*C12Q 1/686* (2018.01)
*B01L 7/00* (2006.01)
(Continued)

(52) U.S. Cl.
CPC ............. *C12Q 1/686* (2013.01); *B01L 7/52* (2013.01); *G01N 21/77* (2013.01);
(Continued)

(58) Field of Classification Search
CPC ............. B01L 7/52; B01L 2200/025; B01L 2200/028; B01L 2300/1844;
(Continued)

(56) References Cited

U.S. PATENT DOCUMENTS

| 3,757,780 A | 9/1973 | Ishikawa |
| 5,151,192 A | 9/1992 | Matkovich et al. |

(Continued)

FOREIGN PATENT DOCUMENTS

| CN | 1680574 A | 10/2005 |
| CN | 1687391 A | 10/2005 |

(Continued)

OTHER PUBLICATIONS

Nov. 9, 2022 Notice of Allowance U.S. Appl. No. 17/479,391.
(Continued)

*Primary Examiner* — Shogo Sasaki
(74) *Attorney, Agent, or Firm* — WILSON SONSINI GOODRICH & ROSATI

(57) ABSTRACT

An analytic device comprising a device housing, a dock to receive a camera enabled mobile electronic device, such as a smartphone and other smart devices, and a processing device to communicate with the mobile electronic device and to control a condition of the assay tube, such as temperature. In another example, the analytic device comprises a device housing and a circuit board. A processing device, a heating block defining a recess to support assay tube, and a resistive heater are surface mounted to the circuit board. A light source and a fan are also provided. A dock may be provided to support a mobile electronic device. The mobile electronic device communicates with the processing device to cause the application of reaction conditions to the assay tube, to perform a PCR procedure, for example. Methods are also disclosed.

20 Claims, 26 Drawing Sheets

Related U.S. Application Data continuation of application No. 15/436,080, filed on Feb. 17, 2017, now Pat. No. 10,457,983, which is a continuation of application No. 14/159,844, filed on Jan. 21, 2014, now Pat. No. 9,579,655.

(60) Provisional application No. 61/754,472, filed on Jan. 18, 2013.

(51) Int. Cl.
  *G01N 21/77* (2006.01)
  *G01N 35/00* (2006.01)

(52) U.S. Cl.
  CPC .. *G01N 35/00871* (2013.01); *B01L 2200/025* (2013.01); *B01L 2200/028* (2013.01); *B01L 2200/147* (2013.01); *B01L 2300/023* (2013.01); *B01L 2300/0609* (2013.01); *B01L 2300/0627* (2013.01); *B01L 2300/0654* (2013.01); *B01L 2300/0832* (2013.01); *B01L 2300/1805* (2013.01); *B01L 2300/1822* (2013.01); *B01L 2300/1827* (2013.01); *B01L 2300/1844* (2013.01); *B01L 2300/1894* (2013.01); *G01N 2021/7786* (2013.01); *G01N 2035/00366* (2013.01); *G01N 2035/00445* (2013.01); *G01N 2035/00881* (2013.01)

(58) Field of Classification Search
  CPC ..... B01L 2300/0627; B01L 2300/1822; B01L 2300/1827; B01L 2200/147; C12Q 1/686; H04W 88/06
  USPC .......................................... 422/82.05, 556.1
  See application file for complete search history.

(56) References Cited

U.S. PATENT DOCUMENTS

| | | | |
|---|---|---|---|
| 5,529,391 A | 6/1996 | Kindman et al. |
| 5,616,301 A | 4/1997 | Moser et al. |
| 5,626,567 A | 5/1997 | Gmeiner |
| 5,849,488 A | 12/1998 | Alatossava et al. |
| 6,274,371 B1 | 8/2001 | Colpan |
| 6,746,864 B1 | 6/2004 | McNeil et al. |
| 7,167,755 B2 | 1/2007 | Seeberger et al. |
| 7,759,112 B2 | 7/2010 | Belgrader |
| 8,361,316 B2 | 1/2013 | Siddiqi |
| 8,454,892 B1 | 6/2013 | Rychwalski et al. |
| 8,633,032 B2 | 1/2014 | Akashi et al. |
| 8,940,524 B2 | 1/2015 | Cobb |
| 9,314,570 B2 | 4/2016 | Kim |
| 9,535,676 B1 | 1/2017 | Forehand et al. |
| 9,575,655 B2 | 2/2017 | Rytivaara |
| 9,579,655 B2 | 2/2017 | Dejohn et al. |
| 9,618,139 B2 | 4/2017 | Handique |
| 9,926,553 B2 | 3/2018 | Dejohn et al. |
| 10,036,058 B2 | 7/2018 | Baumgartner et al. |
| 10,457,983 B2 | 10/2019 | Dejohn et al. |
| 10,724,032 B2 | 7/2020 | Dejohn et al. |
| 11,299,728 B2 | 4/2022 | Dejohn et al. |
| 2001/0003652 A1 | 6/2001 | Freeman |
| 2001/0007062 A1 | 7/2001 | Dumaresq-Lucas et al. |
| 2001/0012612 A1 | 8/2001 | Petersen et al. |
| 2002/0150907 A1 | 10/2002 | Fomovskaia et al. |
| 2004/0126279 A1 | 7/2004 | Renzi et al. |
| 2004/0208796 A1 | 10/2004 | Chiga |
| 2005/0033196 A1* | 2/2005 | Alroy ............... A61B 5/150824 600/583 |
| 2006/0001870 A1 | 1/2006 | Voigt et al. |
| 2006/0213827 A1 | 9/2006 | Nozaki |
| 2006/0216206 A1 | 9/2006 | Hudson et al. |
| 2006/0222567 A1* | 10/2006 | Kloepfer ............. G01N 21/8483 422/68.1 |
| 2007/0035732 A1 | 2/2007 | Marsche et al. |
| 2007/0122809 A1 | 5/2007 | Stevenson et al. |
| 2008/0145848 A1 | 6/2008 | Stephan et al. |
| 2008/0145858 A1 | 6/2008 | Kim et al. |
| 2008/0254532 A1 | 10/2008 | Chang et al. |
| 2009/0111193 A1 | 4/2009 | Cooney et al. |
| 2009/0142333 A1 | 6/2009 | Knopf et al. |
| 2009/0143233 A1 | 6/2009 | Knight et al. |
| 2010/0177950 A1* | 7/2010 | Donovan ............... G16H 50/30 702/19 |
| 2010/0204462 A1 | 8/2010 | Walter et al. |
| 2011/0057117 A1 | 3/2011 | Fawcett et al. |
| 2011/0076735 A1 | 3/2011 | Jovanovich et al. |
| 2011/0201099 A1 | 8/2011 | Anderson et al. |
| 2011/0290647 A1 | 12/2011 | Feiglin |
| 2012/0077259 A1 | 3/2012 | Cobb |
| 2012/0220024 A1 | 8/2012 | Cobb |
| 2012/0288892 A1 | 11/2012 | Maiyuran et al. |
| 2012/0288897 A1 | 11/2012 | Ching et al. |
| 2013/0028814 A1 | 1/2013 | Numai |
| 2013/0078619 A1 | 3/2013 | Cooney et al. |
| 2013/0115607 A1 | 5/2013 | Nielsen et al. |
| 2013/0230845 A1 | 9/2013 | Egan et al. |
| 2014/0008311 A1 | 1/2014 | Weston et al. |
| 2014/0206412 A1 | 7/2014 | Dejohn et al. |
| 2015/0024436 A1 | 1/2015 | Eberhart et al. |
| 2015/0111287 A1 | 4/2015 | Rawle |
| 2015/0126724 A1 | 5/2015 | Dejohn et al. |
| 2016/0041095 A1 | 2/2016 | Rothberg et al. |
| 2016/0069921 A1 | 3/2016 | Holmes et al. |
| 2016/0115520 A1 | 4/2016 | Krishnamurthy |
| 2016/0155120 A1 | 6/2016 | Hurry |
| 2016/0169924 A1 | 6/2016 | Torgerson et al. |
| 2016/0230210 A1 | 8/2016 | Chen et al. |
| 2016/0231171 A1 | 8/2016 | Assefa et al. |
| 2016/0265040 A1 | 9/2016 | Baumgartner et al. |
| 2017/0068533 A1 | 3/2017 | Kiaie et al. |
| 2017/0183713 A1 | 6/2017 | Dejohn et al. |
| 2017/0327867 A1 | 11/2017 | Dohale et al. |
| 2017/0333894 A1 | 11/2017 | Khalid et al. |
| 2020/0276582 A1 | 9/2020 | Dejohn et al. |
| 2020/0376494 A1 | 12/2020 | Dejohn et al. |
| 2022/0074847 A1 | 3/2022 | Eisenhower et al. |
| 2022/0186325 A1 | 6/2022 | Dejohn et al. |
| 2022/0315916 A1 | 10/2022 | Dejohn et al. |

FOREIGN PATENT DOCUMENTS

| | | |
|---|---|---|
| CN | 101722071 A | 6/2010 |
| CN | 101868721 A | 10/2010 |
| CN | 102348985 A | 2/2012 |
| CN | 102472695 A | 5/2012 |
| CN | 202379991 U | 8/2012 |
| CN | 104919035 A | 9/2015 |
| CN | 105092543 A | 11/2015 |
| EP | 0471721 B1 | 4/1995 |
| EP | 0781291 B1 | 12/2004 |
| EP | 1704922 A2 | 9/2006 |
| EP | 2174715 A1 | 4/2010 |
| EP | 2695629 A2 | 2/2014 |
| EP | 3063524 | 1/2020 |
| EP | 3685918 A1 | 7/2020 |
| GB | 2344526 A | 6/2000 |
| JP | 2013525763 A | 6/2013 |
| JP | 2016527510 A | 9/2016 |
| TW | 207958 B | 6/1993 |
| TW | 201144037 A | 12/2011 |
| WO | WO-2004045772 A2 | 6/2004 |
| WO | WO-2009036956 A1 | 3/2009 |
| WO | WO-2009047804 A2 | 4/2009 |
| WO | WO-2011106315 A1 | 9/2011 |
| WO | WO-2011106384 A1 | 9/2011 |
| WO | WO-2011130629 A1 | 10/2011 |
| WO | WO-2012138177 A2 | 10/2012 |
| WO | WO-2013010178 A1 | 1/2013 |
| WO | WO-2013052318 A1 | 4/2013 |
| WO | WO-2014100725 A1 | 6/2014 |
| WO | WO-2014113785 A1 | 7/2014 |
| WO | WO-2015015175 A1 | 2/2015 |
| WO | WO-2015054245 A1 | 4/2015 |

(56) References Cited

FOREIGN PATENT DOCUMENTS

| WO | WO-2015066540 A1 | 5/2015 |
|---|---|---|
| WO | WO-2016124907 A1 | 8/2016 |
| WO | WO-2017112911 A1 | 6/2017 |
| WO | WO-2019055875 | 3/2019 |
| WO | WO-2019055875 A2 | 3/2019 |
| WO | WO-2019118343 A2 | 6/2019 |
| WO | WO-2019143812 A1 | 7/2019 |
| WO | WO-2020191193 A1 | 9/2020 |
| WO | WO-2020257297 A1 | 12/2020 |
| WO | WO-2022061105 A1 | 3/2022 |

OTHER PUBLICATIONS

Dec. 17, 2021 Non-Final Office Action U.S. Appl. No. 16/817,733.
Feb. 1, 2023 Notice of Allowance U.S. Appl. No. 16/571,535.
Mar. 29, 2022 Final Office Action U.S. Appl. No. 16/571,535.
Jun. 15, 2022 Non-Final Office Action U.S. Appl. No. 16/899,810.
Jun. 29, 2022 Non-Final Office Action U.S. Appl. No. 17/479,391.
Aug. 23, 2021 Non-Final Office Action U.S. Appl. No. 16/898,865.
Aug. 8, 2022 Final Office Action U.S. Appl. No. 16/817,733.
Sep. 15, 2021 Non-Final Office Action U.S. Appl. No. 16/571,535.
Sep. 30, 2022 Final Office Action U.S. Appl. No. 16/571,535.
Corrected Notice of Allowability dated Jun. 30, 2020 for U.S. Appl. No. 15/682,675.
European Examination Report dated Aug. 4, 2021, for EP Application No. 18888874.7.
European Examination Report dated Oct. 8, 2018, for EP Appl. 14740636.7.
European search report and search opinion dated Jun. 22, 2017 for EP Application No. EP14859198.5.
European search report with written opinion dated Aug. 22, 2016 for EP14740636.
Extended European Search Report dated Oct. 14, 2022 for EP20774341.0.
Extended European Search Report dated Apr. 28, 2020 for EP Application No. EP19216171.9.
Extended European Search Report dated Apr. 9, 2021 for EP Application No. EP18857231.
Extended European Search Report dated Jun. 7, 2022 for EP Application No. EP21210493.9.
International preliminary report on patentability and search report dated Dec. 3, 2015 for PCT Application No. PCT/US14/63552.
International Preliminary Report on Patentability dated Mar. 26, 2020 for PCT Application No. PCT/US2018/051228.
International Preliminary Report on Patentability dated Jul. 21, 2015 for International Application No. PCT/US2014/012308.
International Preliminary Report on Patentability dated Jul. 21, 2020 for International Application No. PCT/US2019/014005.
International Preliminary Report on Patentability dated Jun. 16, 2020 for International Application No. PCT/US2018/064736.
International Preliminary Report on Patentability for corresponding PCT Application No. PCT/US2020/023630 issued Sep. 30, 2021.
International Preliminary Report on Patentability for PCT/US2020/038159 issued Dec. 30, 2021.
International Search Report and Written Opinion dated Apr. 2, 2019 for PCT/US1851228.
International Search Report and Written Opinion dated May 23, 2019 for International Application No. PCT/US2019/014005.
International Search Report and Written Opinion for corresponding PCT Application No. PCT/US2020/023630 issued Jun. 16, 2020.
International Search Report and Written Opinion for PCT/US2020/038159 issued Oct. 14, 2020.
International Search Report and Written Opinion for PCT/US2021/050862 issued Dec. 30, 2021.
International Search Report dated Jan. 21, 2015 for PCT Application No. PCT/US14/63552.
International search report with written opinion dated May 23, 2014 for PCT/US2014/012308.
ISR/WO dated Apr. 19, 2019 for PCT/US18/064736.
ISR/WO dated May 23, 2019 for PCT/US19/14005.
Non-Final Office Action dated Sep. 4, 2019 for U.S. Appl. No. 15/682,675.
Notice of allowance dated Jan. 2, 2018 for U.S. Appl. No. 14/530,449.
Notice of allowance dated Jan. 17, 2017 for U.S. Appl. No. 14/159,844.
Notice of allowance dated Oct. 12, 2016 for U.S. Appl. No. 14/159,844.
Notice of allowance dated Dec. 8, 2021 for U.S. Appl. No. 16/898,865.
Notice of allowance dated Sep. 11, 2019 for U.S. Appl. No. 15/436,080.
Notice of allowance dated Sep. 27, 2019 for U.S. Appl. No. 15/436,080.
Notice of Allowance dated Jan. 30, 2018 for U.S. Appl. No. 14/530,449.
Notice of Allowance dated Mar. 18, 2020 for U.S. Appl. No. 15/682,675.
Office action dated Mar. 25, 2016 for U.S. Appl. No. 14/530,449.
Office action dated May 5, 2017 for U.S. Appl. No. 14/159,844.
Office action dated Jun. 20, 2017 for U.S. Appl. No. 14/530,449.
Office action dated Aug. 10, 2016 for U.S. Appl. No. 14/530,449.
Office action dated Nov. 5, 2015 for U.S. Appl. No. 14/159,844.
Office Action dated Jul. 27, 2016 issued in the corresponding Chinese Patent Application No. 201480010760.9.

* cited by examiner

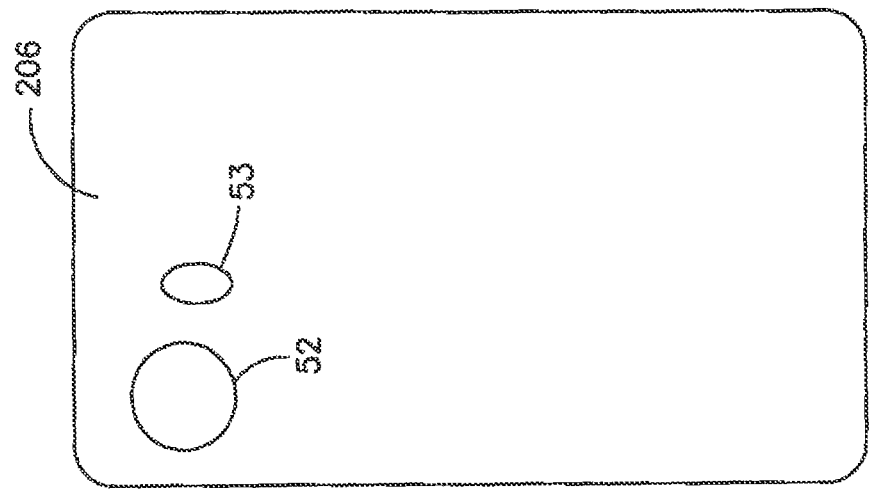
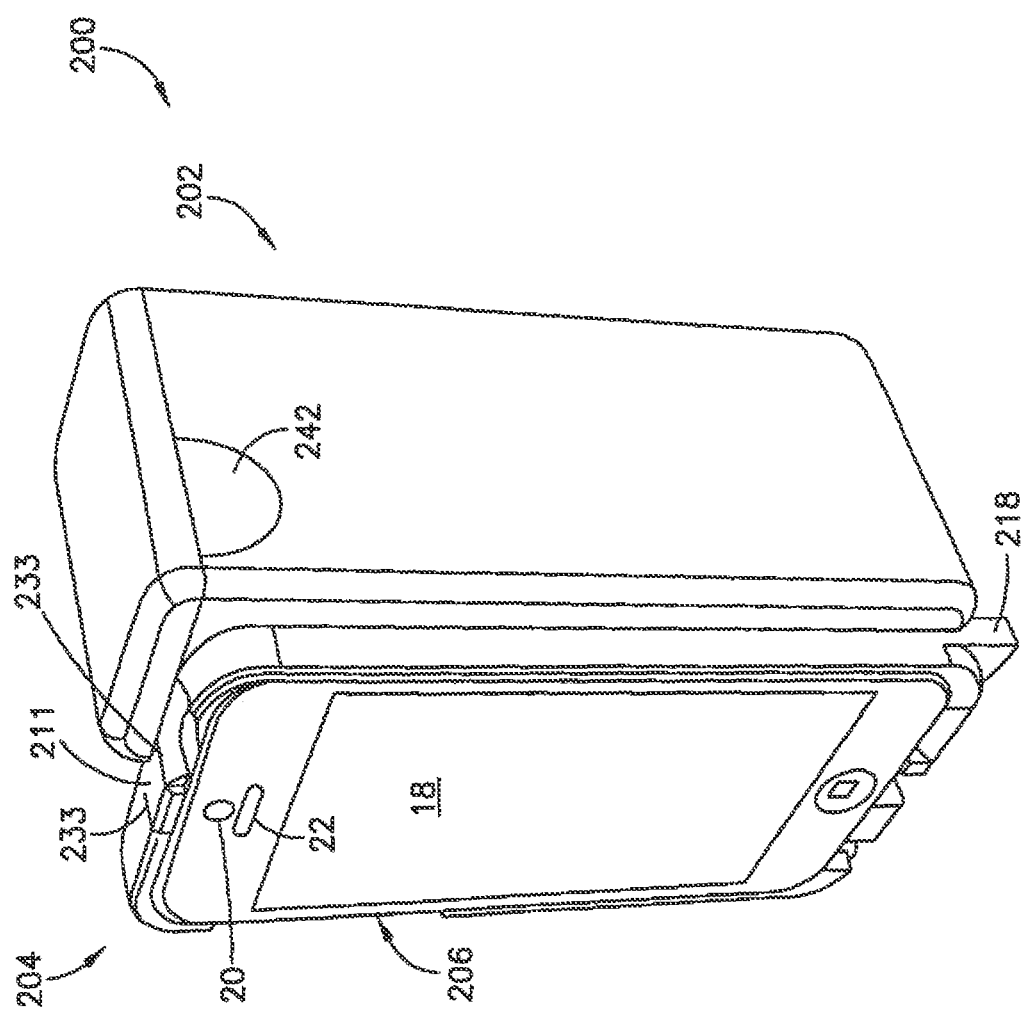
FIG. 7b
FIG. 7a

ANALYTIC DEVICE

RELATED APPLICATIONS

This application is a divisional of Ser. No. 16/571,535, filed Sep. 16, 2019, now U.S. Pat. No. 11,667,963, which is a continuation of U.S. application Ser. No. 15/436,080, filed Feb. 17, 2017, now U.S. Pat. No. 10,457,983, which is a continuation of U.S. application Ser. No. 14/159,844, filed Jan. 21, 2014, now U.S. Pat. No. 9,579,655, which claims the benefit of U.S. Provisional Patent Application No. 61/754,472, which was filed on Jan. 18, 2013, all of which are assigned to the assignee of the present invention and are incorporated by reference herein.

FIELD OF THE INVENTION

Embodiments of the invention relate to analytic devices and, more particularly, to an analytic device including a docking station to receive a camera enabled, mobile electronic device, such as a smartphone.

BACKGROUND OF THE INVENTION

Assay instrumentation enables the interrogation of biological and chemical samples to identify components of the sample. The sample may be processed prior to performing the assay. The processed sample or assay may be placed in an assay tube and positioned in an internal compartment of a device for performing the assay and obtaining the results. The assay procedure may include the application of light, heat, enzymes, etc. The instrumentation includes computing and display components. The computing system controls the instrumentation and processing of gathered data. The display provides a graphical representation of the measured data. The cost and bulk of such instrumentation systems, such as medical diagnostic equipment or genetic testing equipment, commonly requires that biological samples be shipped to a testing facility for processing and analysis. This delays the receipt of test results, often by several days.

The nucleic acids DNA and RNA may be extracted from a biological sample in accordance with the Boom method or modifications thereof, for example, as is known in the art. In accordance with the Boom method, a biological sample is lysed and/or homogenized by mixing the biological sample with detergent in the presence of protein degrading enzymes. The chaotropic agents and silica or silica coated beads are mixed with the lysed biological sample. The chaotropic agents disrupt and denature the structure of nucleic acids by interfering with the macromolecular interactions mediated by non-covalent forces, such as hydrogen bonding, van der Waals forces, and hydrophobic interactions, for example. In the presence of the chaotropic agents, water is removed from the phosphate groups of the nucleic acids, exposing them and allowing hydrophobic bonding to the silica, such as silica or silica coated beads. Protein, cellular debris, and other substances in the biological samples do not bond to the silica and are retained in the solution. The silica beads are washed several times to remove non-nucleic acid materials, such as proteins, lipids, cellular constituents, including cellular molecules, and other substances found in biological samples. Silica coated magnetic beads may be used to assist in the separation of the nucleic acids bound to the silica coating from the solution, via a magnetic field or magnet. The nucleic acids are then eluted from the silica or silica coated beads into a buffer by decreasing the concentration of the chaotropic agents. The elution buffer may be pure water or Tris EDTA ("TE") buffer, for example.

Polymerase chain reaction ("PCR") is a biochemical process used in assay procedures to exponentially copy a target nucleic acid (DNA or RNA) sequence. The PCR process can be tailored to be highly specific and sensitive, allowing amplification of a low copy number sequence into a detectable quantity. The reaction requires a combination of a target nucleic acid sequence, a DNA polymerase, a primer (short DNA sequence that hybridizes to a target sequence complementary to the target DNA), deoxynucleotide triphosphates ("dNTPs") (which are joined by the polymerase to the copied sequences), and a buffer solution including divalent cations (magnesium or manganese ions). The reaction proceeds in temperature cycles including: 1) a melting/denaturing stage during which the reaction mixture is brought to a relatively high temperature at which double stranded DNA separates into single strands; and 2) a lower annealing temperature, at which the primers attach to a complementary sequence and the polymerase join the dNPT to the 3' end of the primer, forming a complimentary copy of the sequence. This copy can then act as a template for subsequent reaction cycles. Additional heating and cooling steps may be provided to optimize the process. The high sensitivity of PCR allows use in a diagnostic assay for detection of a pathogen without culturing, as may be required in alternative assays. The high sensitivity also reduces false negatives. The high specificity of PCR reduces false positives.

Quantitative Real-Time PCR (qPCR) is the real time detection of an amplified DNA or RNA sequence. This process can use intercalating dyes that fluoresce when exposed to an excitation wavelength after the dye binds to double stranded DNA. Alternatively, other chemistries are available, such as linear probes. Probe chemistries add another layer of specificity because specific hybridization between the probe and a target nucleic acid sequence is required to generate fluorescence.

One example of a linear probe is a hydrolysis probe, which are nucleic acid sequences that include a reporter dye, such as a fluorophore, on the 5' end, and a fluorescent quenching moiety agent on the 3' end. Such a probe generally relies on the 5'-3' exonuclease activity of Taq Polymerase. The fluorescent quenching of the 5' fluorophore requires that the quenching agent be in proximity of the 5' fluorophore. The polymerase hydrolyzes the 5' fluorophore during the extension phase of a PCR cycle, the fluorophore is removed from proximity to the quenching agent, allowing fluorescence from the dye to be detected. As in other real-time PCR methods, the resulting fluorescence signal permits quantitative measurements of the accumulation of the product during the exponential stages of the PCR.

Another probe chemistry that can be used are structured probes, such as molecular beacons. Molecular Beacons consist of a hairpin loop structure that is complementary to the target sequence and a stem complementary to the termini. One end of the termini contains a reporter dye and the other end contains a quencher dye which are brought in close proximity when the probe is in the hairpin state. Upon binding to its target the hairpin is opened and the fluorophore and quencher are separated, resulting in increased fluorescence. If the target sequence does not exactly match the Molecular Beacon sequence, hybridization and therefore fluorescence will not occur because the hairpin state is thermodynamically favored over the hybridized state.

qRT-PCR (Real Time quantitative Reverse Transcription PCR) enables reliable detection and measurement of RNA targets, such as mRNA and RNA viruses. An initial cycle of the reaction employs a reverse transcriptase to make a DNA copy from an RNA template. The copies of the DNA sequence are then amplified as with conventional PCR.

The functionality of personal electronic devices, such as smartphones and tablets, for example, is expanding. For example, smartphones are capable of wireless data transmission, global position tracking, image and video capture from front and rear facing cameras, data processing, data storage (including image storage), data display, time and date tracking, and acceleration measuring, for example.

Smartphones have been used in conjunction with medical devices for data collection and analysis. For example, Alive-Cor, Inc., San Francisco, California, provides an iPhone 4, 4S, and 5 case with a built-in heart monitor that enables performance of an electrocardiogram (ECG). The iPhone ECG can be used by consumers, for clinical diagnostics and in veterinary applications. iBGStar®, available from the Sanofi Aventis Groupe, Frankfurt, Germany, provides a glucose meter for diabetics that plugs into the bottom of an iPhone. Mobisante, Inc., Redmond, Washington, has developed a handheld, smartphone-enabled ultrasound imaging device. CellScope, Inc., San Francisco, California, developed a smart-phone enabled otoscope for remote diagnoses of ear conditions, such as pediatric ear infections. Tinke, available from Zensorium, Singapore, monitors pulse, respiration, and blood oxygen levels. An iPhone App also displays pulse, respiration, and blood oxygen measurements, as well as composite score related to fitness and wellness of a user.

SUMMARY OF THE INVENTION

In accordance with an embodiment of the invention, an analytic device includes an analytic unit and a docking station or dock to temporarily or permanently hold a camera enabled, mobile electronic device. The docking station or dock is a support that may be attached to an external portion of the analytic unit, may be a part of the housing of the analytic unit, or may be internal to the analytic unit. The docking station and/or the analytic unit have a window positioned so that when the mobile electronic device is held in the docking station, a camera on the camera enabled mobile electronic device, such as a back facing camera, is aligned with the window in order to capture images within in the interior of the analytic unit. An assay tube holding an assay to be analyzed is supported within the analytic unit. The assay tube is positioned within the analytic unit so that the mobile electronic device can capture images of the assay within assay tube when the mobile electronic device is supported by the docking station. The assay tube may be supported in a controllable assay chamber that allows the sample to be subjected to reaction conditions, such as heating and cooling, for example, prior to image capture. The application of reaction conditions may be performed by the analytic device under at least partial control of the mobile electronic device. The camera enabled mobile electronic device may be a smartphone, tablet, or iPod®, or other such smart device that includes at least one camera. The reaction conditions may define a PCR procedure to identify the presence of a target nucleic acid sequence, such as a nucleic acid sequence of a target virus or bacteria, for example.

In one embodiment, a sample heater is positioned within the housing to heat the assay tube and the assay within the assay tube. The heater may be a hot air heater including a fan to blow the hot air toward the assay tube. In another example, the heater is a heating block that is heated by resistive heating and defines one or more recesses to support one or more assay tubes, respectively. In another example, individual heating blocks are provided for each assay tube. In this example, individual resistive heaters may be provided for each heating block. Individual temperature sensors may also be provided for each heating block. A fan or blower may be provided to cool the heating block or blocks.

Also within the housing is a light source positioned to excite the contents of the assay. Respective light sources may be provided for each assay tube, for example. Respective light pipes may be provided to convey the excitation light from each light source to each assay tube. The heating block or blocks described above define openings with respect to respective recesses to allow for excitation of each assay by excitation light and the imaging of each assay by the camera of the mobile electronic device. Increasing fluorescence as the assay is subjected to the reaction conditions, which may be recorded in the images captured by the camera of the mobile electronic device, is indicative of the presence of the target nucleic acid sequence in the assay and the initial concentration or quantity of the target in the sample, for example.

A processing device, such as a microcontroller or microprocessor, is provided in the analytic device to control the heating of the heating block/blocks and the state of the fan (on/off and fan speed, for example), monitor the temperature sensors, receive information and/or instructions from the mobile electronic device, and/or provide information to the mobile electronic device, for example. The heating blocks, resistive heaters, temperature sensors, and/or light sources may be surface mountable components that are surface mounted to a circuit board, such as the circuit board to which the processing device is mounted.

Data exchange electronics, such as wireless communication electronics and/or electrical contacts, may also be provided within the housing to allow commands from the mobile electronic device to be communicated to the components within the housing.

In accordance with another embodiment of the invention, a method for conducting a sample assay is disclosed comprising placing an assay tube containing assay within an analytic device. A signal is provided from a camera enabled mobile electronic device to cause the device to subject the assay mixture container to reaction conditions, such as temperature cycling. The mobile electronic device may be supported by a docking station attached to or part of the analytic device. A camera on the camera enabled mobile electronic device, such as a rear facing camera, captures one or more images of the assay within the housing. The image may capture the fluorescence of target nucleic acids, which is indicative of the presence of the target nucleic acid sequence in the assay. The image may then be processed to generate a data set. The data set may be stored in an electronic memory on the camera enabled mobile electronic device and analyzed by the mobile electronic device or communicated to other devices, via a network, for example. The data set may be wirelessly transferred to another device, for example.

The mobile electronic device may capture or generate other data, as well, to associate with the image. For example, the camera may also detect whether an assay tube is properly positioned and/or filled, premature opening of the lid, and other potential problems. A time stamp or other associated data may be generated from the camera enabled mobile electronic device, such as location, acceleration of the analytic device, temperature, test protocol, etc. Acceleration of the analytic device, which may be determined by accelerometer or gyroscopic sensors in the mobile electronic device, may be used in the quality control (QC) of the assay procedure to determine if the smart phone and/or the analytic device were dropped, inverted, or impacted, for example, which could interfere with the test results due to displacement of the assay in the assay tubes. A warning or system check may be provided by the mobile electronic device to the user if there is a problem. A front facing camera on the camera enabled electronic device may also be used to capture an image of a user running the assay procedure, or scan a sample container or a label on reagents to store assay information with the collected data, while the mobile electronic device is in the docking station. The assay procedure may be PCR, for example.

In accordance with one embodiment of the invention, an analytic device is disclosed comprising a device housing and a dock on the device housing. The dock is configured to receive a camera enabled, mobile electronic device. A controllable assay chamber is within the housing, configured to support at least one assay tube containing an assay to be analyzed. The analytic device further comprises a processing device configured to communicate with the mobile electronic device and to control at least one condition of the assay tube. At least one of the housing and the dock define a window positioned such that, when a camera enabled, mobile electronic device is received in the dock, a camera on the mobile electronic device is positioned to capture images through the window.

In accordance with another embodiment of the invention, an analytic device is disclosed comprising a device housing, a circuit board within the housing, and a processing device surface mounted to the circuit board. A surface mountable heating block defines a recess to receive an assay tube, and first and second openings. The heating block is surface mounted to the circuit board. A surface mountable resistive heater is surface mounted to the circuit board in thermal contact with the heating block to heat the heating block, under the control of the processing device. A fan is positioned to blow air onto the heating block to cool the heating block, under the control of the processing device. A light source is positioned to expose contents of the assay tube to excitation light through the first opening, under the control of the processing device. The light source may be a surface mountable light source that is also surface mounted to the circuit board. A dock may be connected to or part of the housing to hold a camera enabled mobile electronic device, wherein, when the camera enabled mobile electronic device is placed in the dock, a camera on the device is positioned to allow image capture of at least a portion of the at least one assay tube, through the second opening in the heating block.

The first and second embodiments may further comprise the camera enabled mobile electronic device supported by the docking station. The mobile electronic device may be configured to control at least one reaction condition, such as by controlling operation of the heating unit, the cooling unit, and/or the light source, by providing information and/or instructions to the processing device of the analytic device. The mobile electronic device may be configured to provide the information and/or instructions by a second processing device under the control of an App stored on the mobile electronic device. The App may be configured to cause the second processing device to provide instructions to run a polymerase chain reaction (PCR) procedure.

In accordance with another embodiment of the invention, a method for conducting an assay procedure comprises placing an assay tube containing an assay mixture within an analytic device, and docking a camera enabled, mobile electronic device to the analytic device such that a camera on the mobile electronic device is positioned to record images of the assay within the assay tube. A signal is sent from the docked mobile electronic device to initiate reaction conditions. The assay within the assay chamber is exposed to reaction conditions. At least one image of the assay within the assay chamber is captured by the camera enabled, mobile electronic device. The reaction conditions may include temperature cycling, for example. Parameters for the reaction conditions may be provided by the mobile electronic device to the analytic device. The assay procedure may be a polymerase chain reaction (PCR) procedure, for example.

BRIEF DESCRIPTION OF THE DRAWINGS

FIG. 7a is a perspective view of the compact PCR analytic device of FIG. 8, with a smartphone in the docking station;

FIG. 7b is a rear view of the camera enabled mobile electronic device used in embodiments of the invention;

FIG. 8 is a front view of the PCR analytic device of FIG. 7a;

FIG. 9 is a perspective, partial cross-sectional, partial breakaway view of the PCR analytic device of FIG. 7a;

FIG. 10 is an enlarged perspective view of the upper portion of the analytic unit of FIG. 7a;

DETAILED DESCRIPTION OF THE PREFERRED EMBODIMENTS

In accordance with an embodiment of the invention, a camera enabled mobile electronic device, such as a smartphone, tablet, or iPod®, for example, is used as both a controller for an analytic system and as an imaging component of the analytic system. Since many users will already own a smartphone, tablet, or iPod® that is able to act as the camera enabled mobile electronic device, the cost of the system is greatly reduced. In addition, the mobile electronic device allows communication of collected data for remote processing. As used herein, the term "camera enabled mobile electronic device" or "mobile electronic device" is a consumer electronic device including a camera, a display screen, a processing device, a wireless communication component, and an input component, such as a keyboard and/or a touch screen of the display. The camera may be on an opposite face of the mobile electronic device than the input component. Such a camera is referred to as a "rear facing camera." The mobile electronic device may also include a front facing camera (on the same face as the input component), global position sensors, acceleration sensors and/or tilt (gyroscopic) sensors, a microphone, and/or fingerprint recognition, for example. In another embodiment of the invention, a camera enabled processing device is integral with the analytic unit. The analytic unit may be configured to perform PCR, for example, to identify the presence of a target nucleic acid sequence in an assay. The target nucleic acid sequence may be from a virus or bacteria, for example. Additional applications are discussed below.

Figure 1:
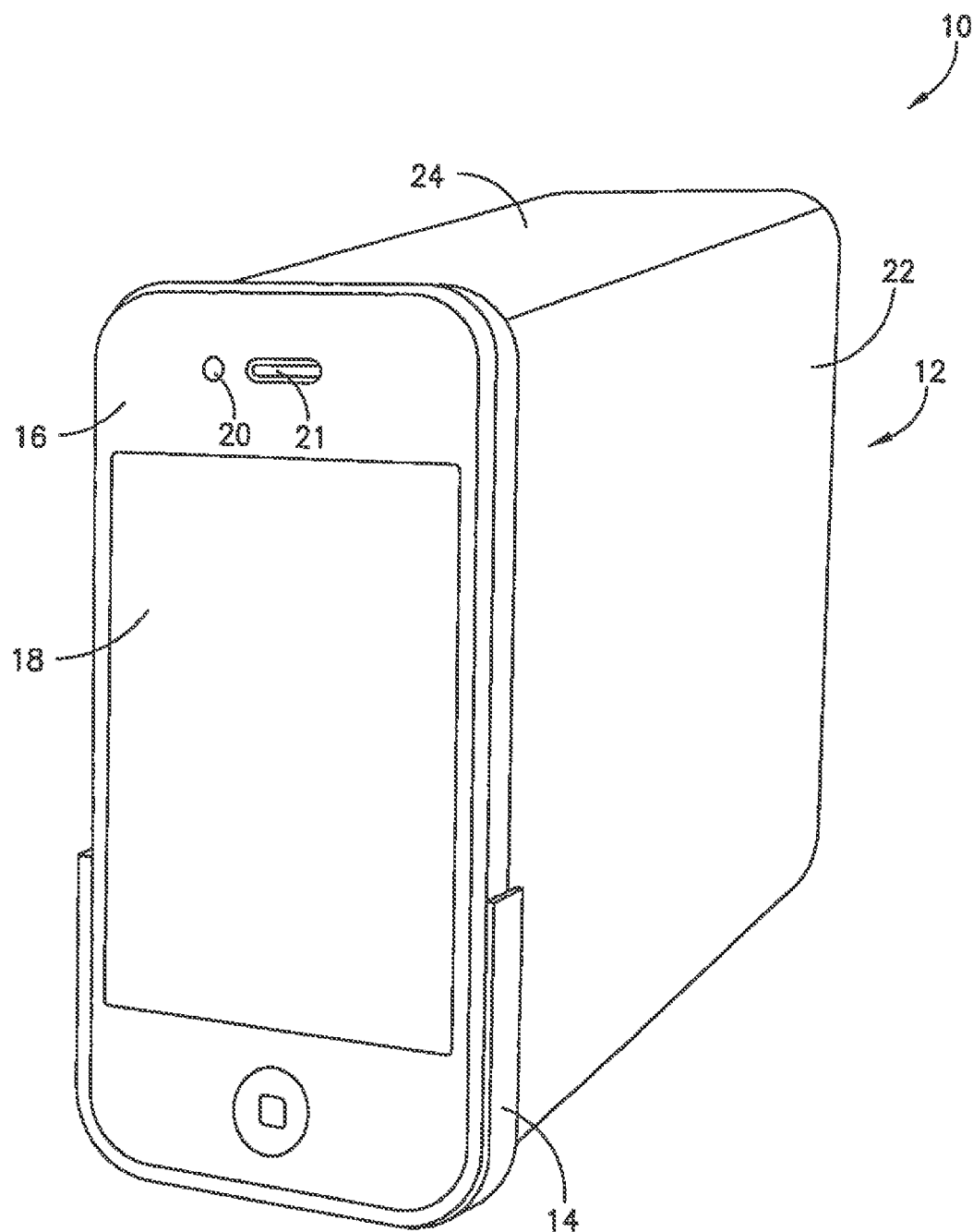
FIG. 1 is a front, perspective view of an embodiment of an analytic device with a smartphone docked to the device, in accordance with an embodiment of the invention.

FIG. 1 shows an example of a desktop PCR analytical device 10 comprising an analytic unit 12 and a docking station or dock 14, in accordance with an embodiment of the invention. In FIG. 1, a camera enabled mobile electronic device 16 is supported in the dock 14. The camera enabled mobile electronic device 16 includes a display screen 18, which may be a touch screen, for the input of instructions. The input of instructions may include the selection of predetermined assay routines, such as one or more PCR routines, stored on the mobile electronic device. In this example, the mobile electronic device 16 also includes a front facing camera 20 and a speaker 21. A speaker is provided at the bottom of the mobile electronic device 16, as well. The front facing camera 20 may be used to capture an image of a code on an assay tube or an assay kit, for example, a code on a reagent container, an image of the user, etc., while the mobile electronic device 16 is supported in the docking station. A rear facing camera 52 shown in FIG. 2, could be used to capture such images prior to docking in the docking station 14. This information may be attached to either a data set or an image from an assay, as discussed below. The speaker 21 can be used to alert a user to an error condition and provide voice instructions for performing the assay, for example.

The analytic unit 12 comprises a housing 22 defined by multiple rectangular walls. The top wall 24 of the housing 22 may comprise a hinged lid that rotates about a hinge (not shown) to open and enable access to the interior of the analytic device 12. A more detailed example of a hinged lid is discussed below with respect to the second embodiment of the present invention. The housing 22 may comprise heat resistant plastic, for example.

Figure 2:
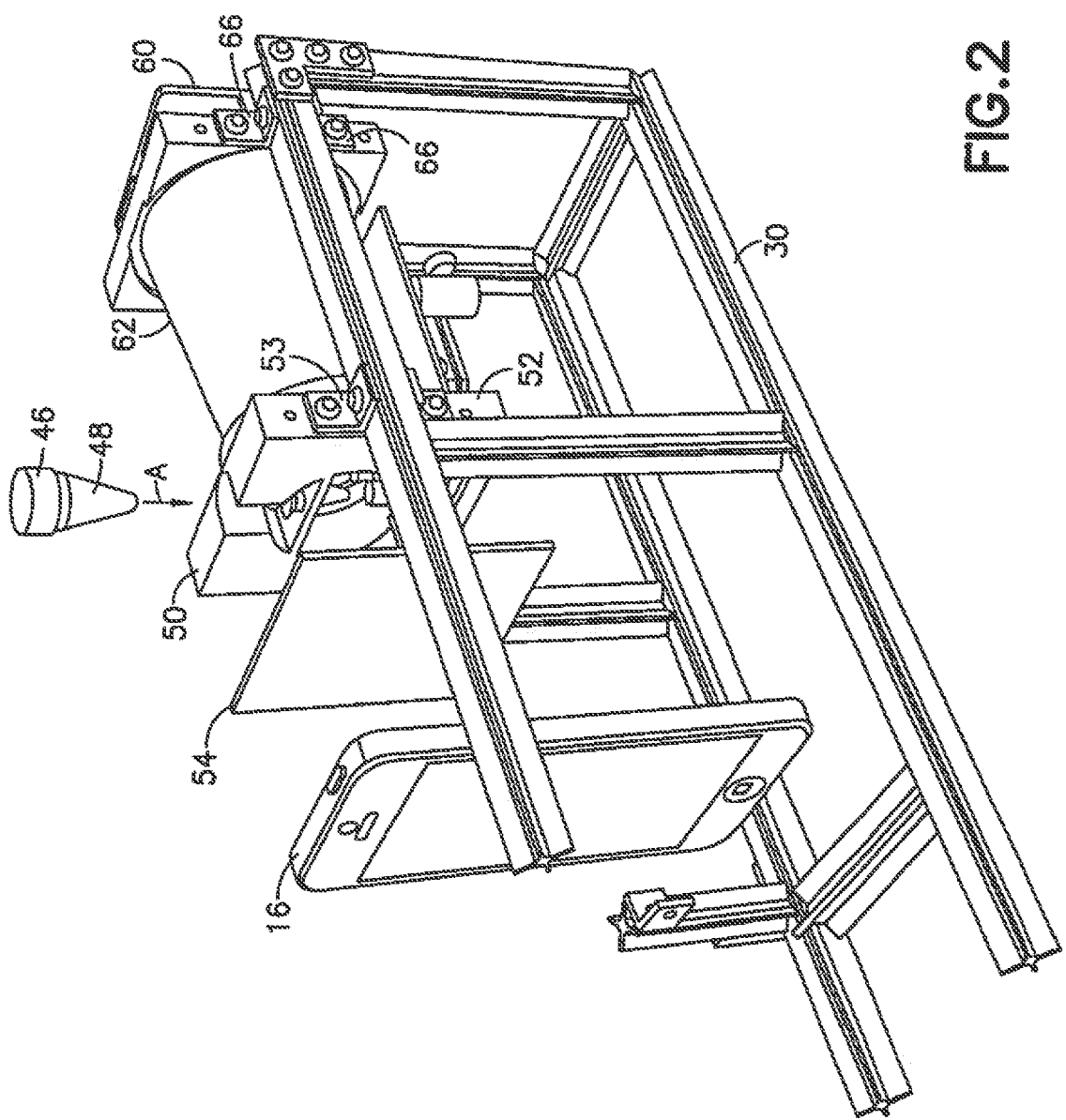
FIG. 2 is a side view of internal components of the analytic device of FIG. 1.

FIG. 2 is a view of the PCR analytic device 10 of FIG. 1, with the housing 22 and the docking station 14 removed. The mobile electronic device 16 is shown in proper relation to the internal components, as if the dock 14 were present. An internal frame 30 directly or indirectly supports the internal components of the analytic unit 12 and the housing 22.

An assay tube 46 containing an assay 48 is shown above an assay tube holder 50. An assay tube 46 is shown in position in the assay tube holder 50, as well. The assay 48 may comprise a mixture of isolated nucleic acid and reagents. Any standard, off the shelf PCR tubes 46 may be used. For example, the assay tube 46 may be a 0.1 ml or 0.2 ml PCR tube, or other thin-walled commercially available PCR tubes. Suitable PCR tubes may be obtained from Phenix Research Products, Candler, North Carolina, for example. The assay tube 46 may be positioned by opening the hinged lid 24, allowing insertion of the assay tube 46 into the assay holder 50. Insertion of the assay tube 46 into the assay holder 50 is indicated schematically by the arrow A.

The assay tube holder 50 in this example is bolted to the frame 30 by brackets 53, two of which are shown in FIG. 2. The assay tube holder 50 and the frame 30 may also be molded plastic and the two components could be molded in one piece.

The mobile electronic device 16 is positioned by the dock 13 so that the rear facing camera 52 (shown in FIG. 3) of the mobile electronic device 16 is positioned to capture images through a transparent heat shield 54. The assay holder 50 defines an open region that allows both heated air and cooling air to circulate about the assay tube 46, and allows light to both excite the assay in the container and be emitted from the assay for detection by the rear facing camera 52.

A blower 60 comprising a fan blows air through a first open end 62a of a compartment 62, allowing controlled heating and cooling of the assay 48 in the assay tube 46, through the second open end 62b of the compartment. The compartment 62 includes a heating coil 64, shown in FIG. 3, which heats air blown through the compartment. The heating coil 64 is activated by applying a voltage to the coil to cause current flow, for example. The compartment 62 is attached to the frame 50 by a bracket 66, two of which are shown in FIG. 2.

Figure 3:
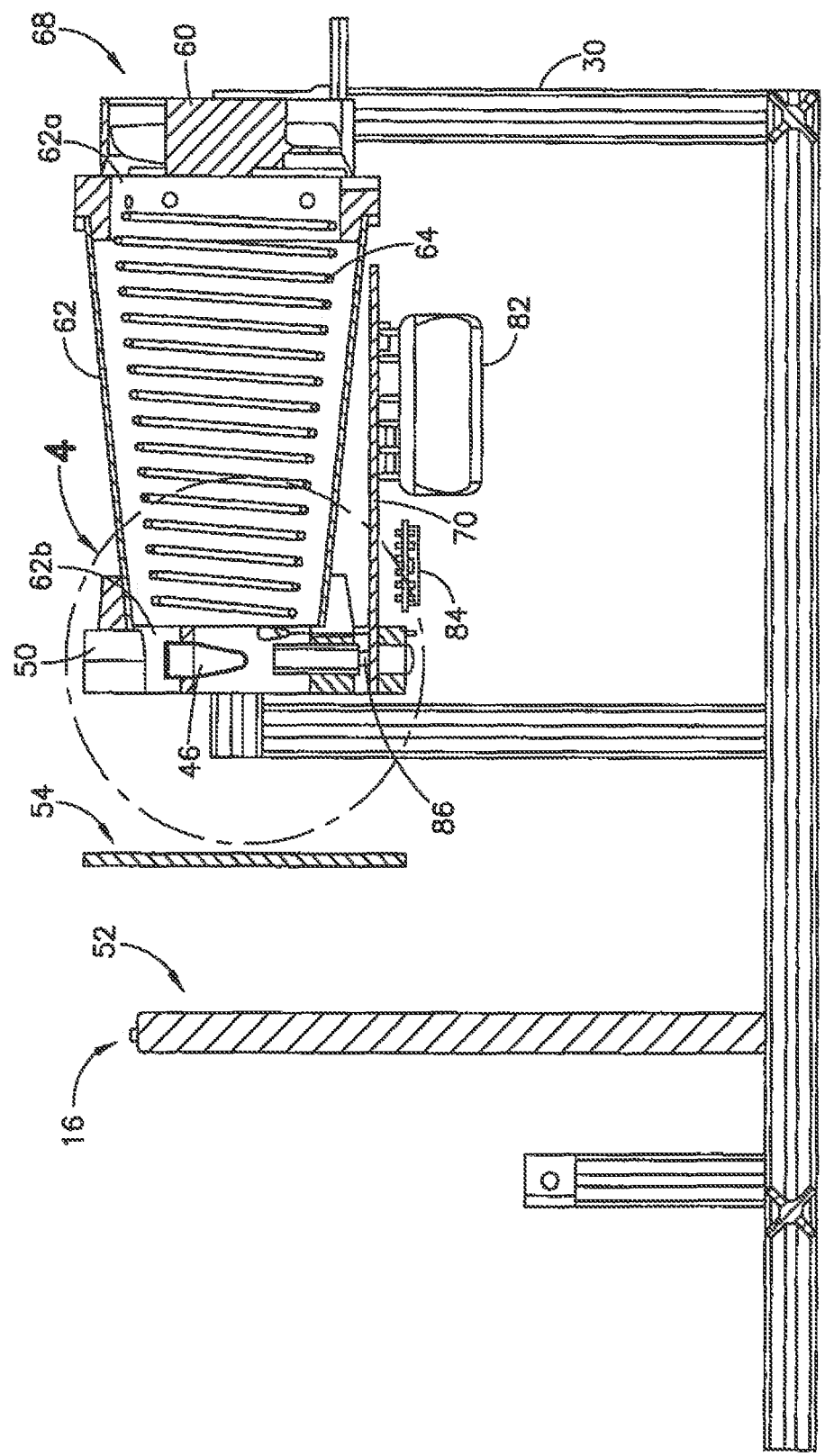
FIG. 3 is a partial cross-sectional, partial breakaway view of the analytic device of FIG. 4.

FIG. 3 is a side, partial cross-sectional view of FIG. 2. The rear facing camera 52, is positioned in the dock 14 it faces the transparent heat shield 40 and is able to the image the assay tube 46 held by the assay holder 42. The heating coil 64 in the compartment 62 is shown. The blower 60 has an intake 68 through which air is drawn into the compartment 62 when the blower is operating.

Also shown in FIG. 3 is a circuit board 70 and a power supply 82 mounted to the circuit board. The power supply 82 may include battery and/or a voltage converter if the analytic device 10 is to be plugged in to line voltage through a socket in a wall, for example. A processing device 84, such as a microcontroller or microprocessor, for example, shown distanced from the circuit board 70 in FIG. 3, is also mounted to the circuit board. A light source 86, such as light emitting diode ("LED"), is also shown mounted to the circuit board 70, below the assay holder 50. The LED acts as an excitation source to excite fluorophores and other markers or dyes in the assay. Memory and other electronic devices (not shown) may also be mounted to the circuit board 70. The circuit board 70 may be connected to the assay holder 50 and to the internal frame 30. Examples of processing devices that may be used are discussed below.

Figure 4:
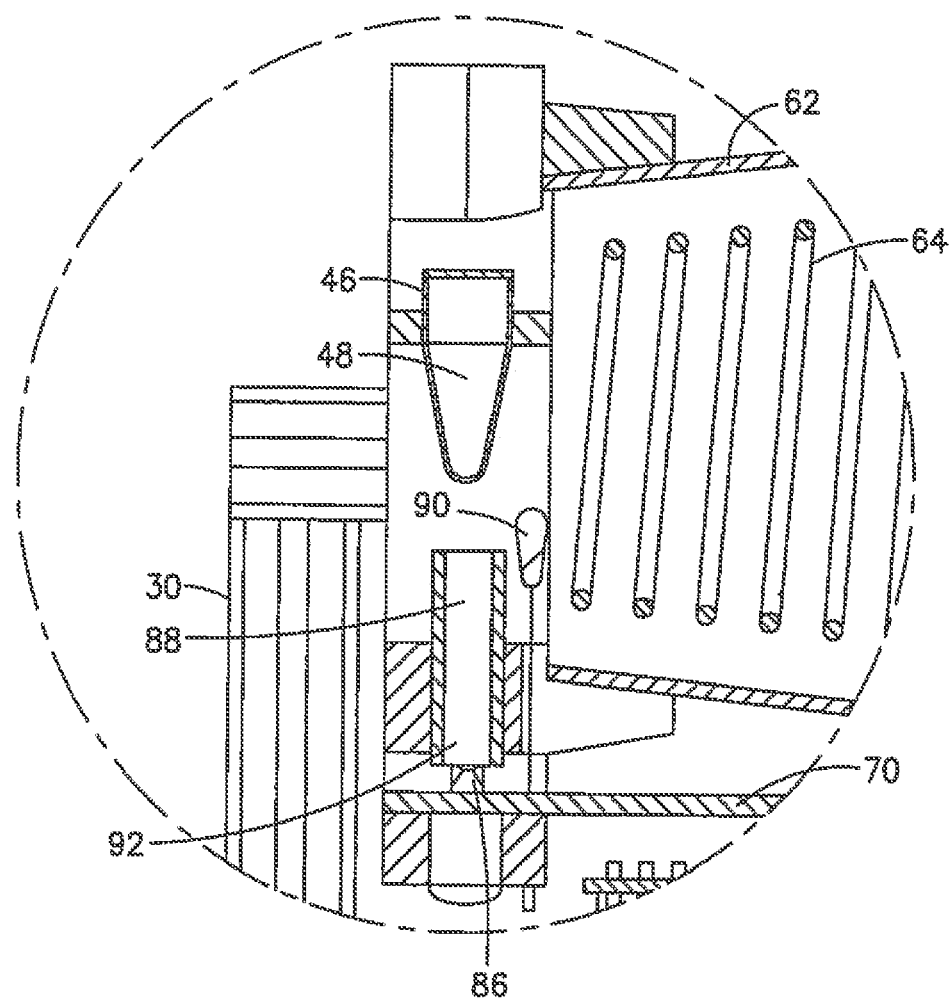
FIG. 4 is an enlarged view of Section X of FIG. 3.

FIG. 4 is an enlarged view of Section X in FIG. 3. The LED 86 directs excitation light though a light pipe 88. The light pipe 88 allows internal reflection of the light from the LED 86 to convey the light to the assay tube 46 and assay 48. The light pipe 92 may be an optical fiber, for example. The heating coil 64 contained within the compartment 60 heats air that is blown by the fan 70 through the heating coil 64. The heated air is blown past the assay tube 46, heating the tube and assay 48. When the heating coil is not activated, the air blown by the blower 60 through the compartment 62 cools the assay tube 46. A temperature probe 90 detects the temperature of the air stream flowing through the compartment 60.

An excitation filter 92 may be placed between the LED 86 and the light pipe 88 to remove light emitted by the LED with a wavelength that overlaps with the wavelength of the assay dye emission. The excitation filter may also be provided between the light pipe 88 and the assay tube 46. In either case, by filtering the light from the LED 86 by the filter 92, the light detected by the camera 52 of the mobile electronic device 16 in the emission band of the dye will be from the dye, not be from the LED 86. For example, if the LED is providing light in a blue wavelength band and the emission dye emits light in a green wavelength band, the filter will remove green light from the light provided by the LED. An emission filter (not shown) may also be provided between the assay tube 48 and the camera to remove light emitted by the LED with a wavelength that overlaps with the wavelength of the light provided by the LED. In this example, it would filter blue light. In this way, the detected light will not be from the LED. An example of an excitation filter and an emission filter are described with respect to the second embodiment. The filters used for a particular assay may depend on the emission dye and LED used.

The temperature probe 90 may also be mounted to a circuit board 70. The processing device 84 controls operation of the heating coil 64, the blower 60, and the LED 86, and receives signals from the temperature probe 90. In particular, the heating coil 64 and the blower 60 are controlled by the processing device 84 to heat and cool the assay tube 46 and the assay 48 to desired temperatures and to maintain the temperatures within desired ranges for desired time intervals during respective assay procedures. The LED 86 is turned on at appropriate times by the processing device 84 to excite the fluorophores and/or other reactants in the assay 48, while the camera 52 images the assay.

Figure 5:
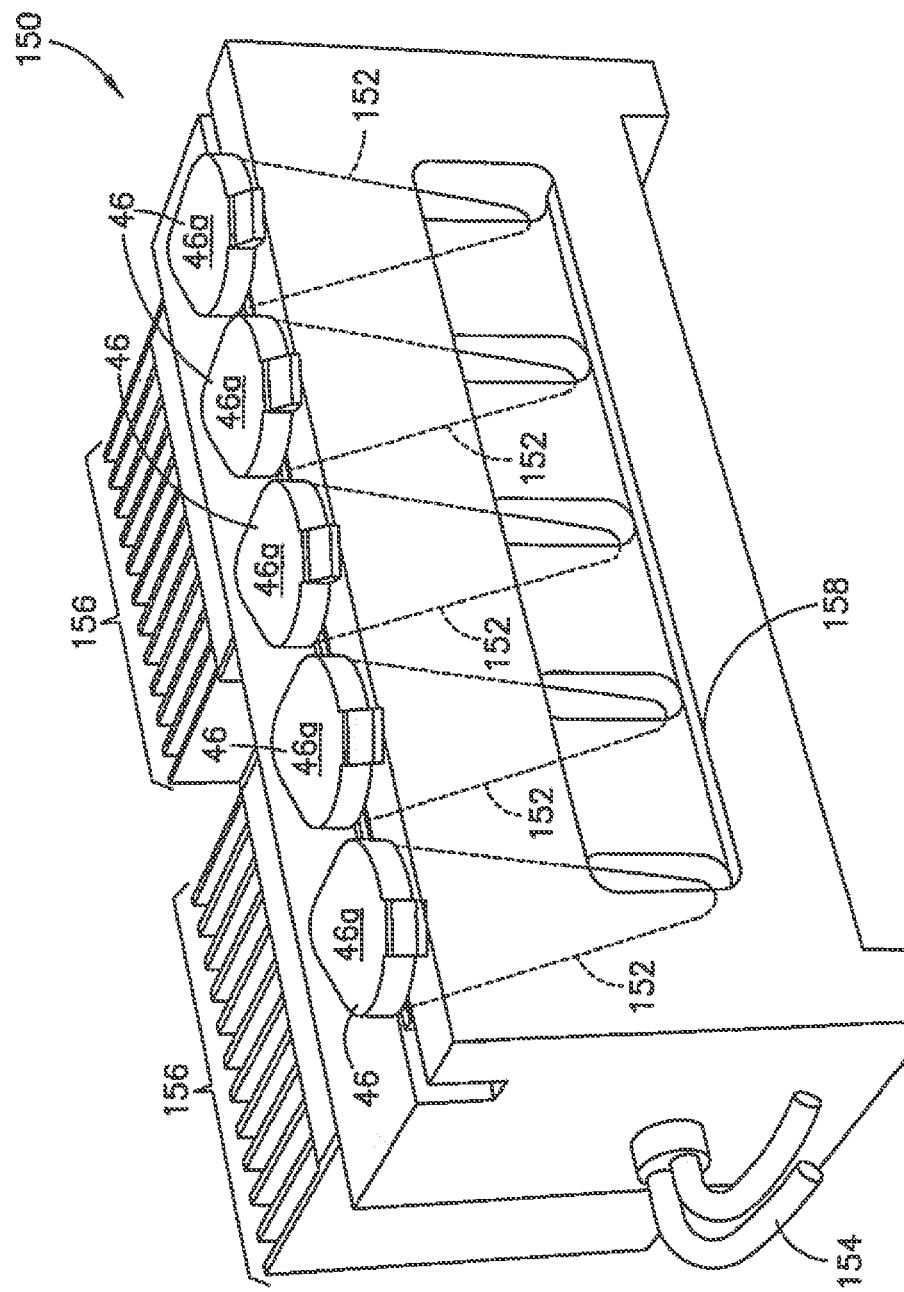
FIG. 5 is a front perspective view of another example of heating block for use with embodiments of the invention.

Instead of the heating coil 64, a heating block 150 may be used, as shown in the perspective view of FIG. 5. In this example, the heating block 150 also functions as the sample holder. The heating block 150 is a solid block of metal or metal alloy, such as aluminum or an aluminum alloy, for example, which is mounted to the frame 30. The heating block 150 may comprise aluminum alloy 6061, for example.

Five recesses (shown in phantom) 152 are defined in the heating block 150. Five assay tubes 46 are shown in the five respective recesses 152. More or fewer recesses may be provided. Tube covers 46a closing each assay tube 46 are shown above the recesses 152. A resistive heating element 154 extends through a length of the block 150, allowing controlled heating of the assay tubes 46 and the assays 48, under the control of the processing device 82. Fins 156 are provided to improve heat dissipation. A fan or blower (not shown), such as the blower 60, may be positioned to face the fins 156 for faster cooling of the fins 156 and the heater block 150, decreasing temperature transition times. The compartment 62 shown in FIGS. 2-4 is not needed when the heating block 150 is used. The use of the heating block 150 provides a more compact footprint than use of the extended compartment 62 and enables heating a number of assay tubes 46 at the same time.

The heating block 150 also defines one or a plurality of openings 158 in front of the recesses 152 to allow for imaging of the assays 48 in the assay tubes 46 by the camera 52. Openings are also provided in the bottom of the heating block 150 (not shown) to allow excitation light to illuminate the assays 46. The heating block 150 may be used in the first embodiment describe above, or in the second embodiment described below.

Assay Example

In the following example, the PCR analytic device 10 in accordance with the first embodiment or the second embodiment discussed below, is used in an assay procedure to observe or identify one or more nucleic acid sequences in an assay. It would be apparent to one of ordinary sill in the art that aspects of this example are also applicable to the second embodiment, described below. The assay may be derived from a human or other animal sample, or a plant sample, for example. The assay may also be derived from an environmental source, such as a water supply, or soil, for example. In one example, the source may be human blood or other tissue sample, for example. Nucleic acid sequences of viruses, bacteria, fungi, protozoa, or invertebrate parasites may be identified in a sample.

The PCR analytic device 10 may also be used in determining human identity, in paternity testing, forensics, defense and homeland security to detect bio-weapons, anti-counterfeiting, plant breeding, food testing, genetically modified organism (GMO) testing, and veterinary testing, for example, as well as in research and education. Examples of particular applications include testing for disease vector organisms, such as a mosquito carrying West Nile Virus; a patient sample in a remote location, such as a test for viral disease; or a livestock borne illness, such as blue tongue in cattle.

Examples of assays that may be performed by the analytic unit 12 include, real-time PCR, immuno PCR, DNA melting curve analysis, and DNA microarrays, for example.

Step One: Scan Kit

In one example, the user places a mobile electronic device 16 in the docking station 14, selects a sample prep kit, and scans a barcode on the kit with the front facing camera 20 of the mobile electronic device 16. A sample prep kit may contain salts, buffers, divalent cations, nucleotides, polymerase enzymes, and linear probes including reporter dyes for identifying one or more target nucleic acid sequences, for example, as is known in the art and discussed above. The reagents may be lyophilized. The one or more target nucleic acid sequences may be indicative of the presence of one or more viruses, bacteria, or other sources of nucleic acid, as discussed above, for example. Sample prep kits for particular nucleic acid sequences are commercially available.

As noted above, if the mobile electronic device 16 has not yet been placed in the dock 14, the rear facing camera 52 may be used. A smartphone 16 will be referred to in this example. Operations of the smartphone 16 are controlled by a processing device, such as a microprocessor, for example, under the control of software, such as a PCR App, for example. PCR Apps may be provided by or downloaded from Biomeme, Inc., Philadelphia, Pennsylvania. The App may cause the processing device of the smartphone 16 to automatically create a new sample profile, generate a unique ID to link the assay with a patient profile, and link the assay with subsequently generated sample, for example. The sample prep kit identification could also be downloaded to a centralized server that could, for instance, track the use of assay kits, inform a user about the number of kits remaining, and/or automatically order new kits if needed.

In addition, the touchscreen on the display screen 18 of the smartphone 16 allows input of patient data, such as age, sex, presence of fever, and other symptoms, for example.

Some data may be auto-populated by the smartphone 16, such as time and date, GPS coordinates, and climate data, for example, under the control of the PCR App.

Step 2: Sample Preparation

A user obtains a test sample, such as a blood or urines sample, in a conventional manner. Nucleic acids may be isolated from the patient sample by any method known in the art, such as the Boom method, discussed above. Pre-isolation processing may be required for certain samples, as is known in the art.

A solution containing isolated nucleic acid sample is introduced into an assay tube 46 containing the reagents in the PCR kit, in lyophilized form. A lid of the assay tube is closed and the tube mixed. The lyophilized reagents in the assay tube 46 dissolve in the solution.

Step 4: Thermal Cycling and Image Capture

In one example, the user places the assay tube 46 containing the assay 48 into the assay holder 42 in the device 12. The smartphone 16 docked in the docking station 14 communicates with the processing device 84 of the PCR device 10, via the PCR App. The PCR App may also cause a Start button to be displayed on the display screen 18, which may be pressed to start the assay procedure. The assay is heated and cooled at different temperatures for predetermined periods of time defined by the PCR protocol being run by the PCR App. At specific times during the assay procedure, the assay is excited by excitation light and images are captured through the viewing window by the back facing camera 52 of the smartphone 16. Increasing fluorescence is indicative of amplification of the target nucleic acid sequence. If the particular target is not present, fluorescence will not increase.

The images may be compared to other captured images or processed by the processing device of the smartphone 16 to extract luminosity data that can be used to determine if the assay shows increased fluorescence, for example, via the PCR App. The data and/or image may then be stored and the image deleted, if desired, to preserve system memory. The images may be displayed on the display screen 18. Alternatively, the processed luminosity values may be displayed on the screen 18, or simply a final result (target present or not present, for example), may be displayed. An example of a thermal cycling/image capture procedure is described in more detail, below.

The App on the smartphone 16 may be configured to cause the processing device of the smartphone 16 to encrypt the assay results, store them on the smartphone 16, and/or upload them to a database, such as a cloud database, if/when the smartphone 16 is within a cellular network, Wifi zone, or other wireless protocol. If the network or Wifi is not available, results may be saved on the smartphone 16 until cellular or Wifi access is available. Uploading to a database preserves memory on the smartphone 16 and/or the analytic device 10. The results may also be automatically sent to the contact information for the patient and/or caretaker, if desired or previously selected.

The patient may also receive or be provided with an option to receive educational information by their own smartphone or by email about the blood borne pathogen they may have been diagnosed with, to educate themselves and learn how to mitigate the severity of the infection, as well as symptoms that might indicate they need to go back and receive follow up care. The patient may be free to access the results via their own smartphone or via a website, along with any doctor or clinician linked with the patient who will be able to advise on further treatment.

Step 5: Disposal

At this point the user is free to dispose of the assay tube 46 and move onto the next test, to start the process again.

In another application, the PCR analytic device 10 may be used to identify DNA tags, which are self-contained authentication labels including a mix of oligonucleotides that provide a unique signal when appropriately interrogated. In the case of anti-counterfeiting, the PCR analytic device 10 acts as a DNA reader, which interrogates a DNA tag to determine its signal and make the association with a unique or known class of signals. DNA tags of a unique sequence can be placed into inks, paints and pharmaceuticals, for example, to create a unique ID for tracking and verifying throughout the supply chain, as is known in the art. One way to read the unique DNA tag is with and primers complementary to the unique DNA tag sequence.

The DNA tag sample collection may comprise dissolving the ink or paint to release the DNA and then capturing that DNA via nucleic acid extraction technologies. Once the pure DNA is isolated it may be placed in an assay tube 46 and a PCR thermal cycling reaction may be run by the analytic device 10, as described above.

In accordance with a second embodiment of the invention, a more compact PCR analytic docking station 200 than the embodiment of FIG. 1 is described with respect to FIGS. 6-19. It will be apparent to one of ordinary skill in the art that aspects of the second embodiment are applicable to the first embodiment and aspects of the first embodiment are applicable to the second embodiment.

Figure 6:
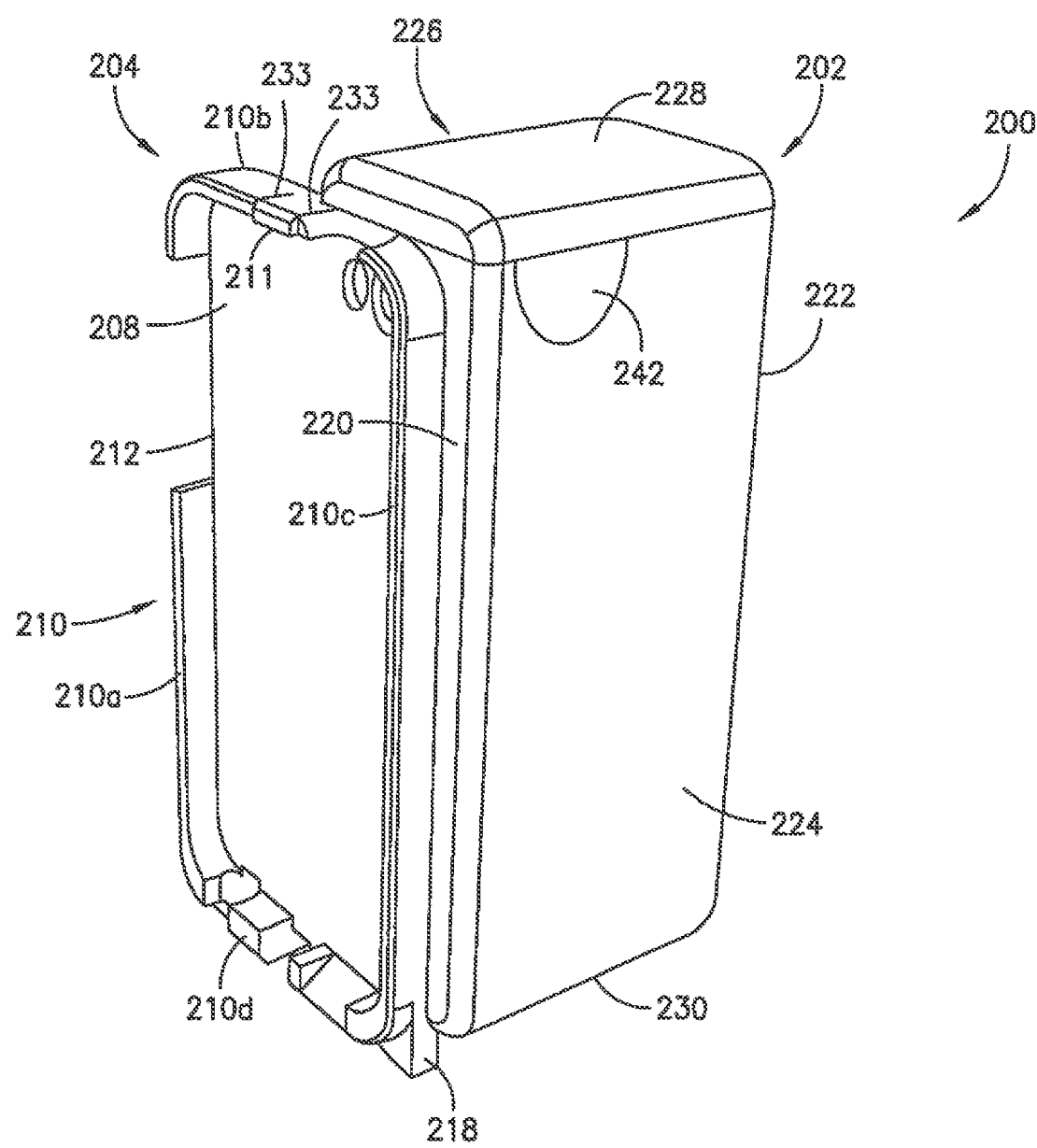
FIG. 6 is a perspective view of an example a compact PCR analytic device in accordance with another embodiment of the invention, without a camera enabled mobile electronic device in the docking station.

FIG. 6 is a perspective view of an example the compact PCR analytic device 200 in accordance with the second embodiment. The device 200 comprises an analytic unit 202 and an external docking station 204 for a camera enabled mobile electronic device 206 (not shown in FIG. 6), such as a smartphone or tablet, for example.

FIG. 7a is a perspective view of the compact PCR analytic device 200 in accordance with the embodiment of FIG. 6, with a smartphone 206 in the docking station 204. The smartphone 206 includes the display 18, the front facing camera 20, the speaker 22, and the rear facing camera 52 discussed above with respect to the mobile electronic device 16 used in the first embodiment. FIG. 7b is a front view of the rear face of the smartphone 206, showing the rear facing camera 52 and a light source 53, such as a flash. The rear facing camera 52, as well as the front facing camera 20, are typically CMOS sensors.

In one example, the analytic unit 202 may have dimensions of about 13.5 cm×4.1 cm×5.8 cm. The analytic device 200 in this example has a weight of about 15.8 ounces with the smartphone 206 in the docking station 204 and about 11.5 ounces without the smartphone in the docking station 204. The PCR analytic device 200 may be handheld and/or may sit on a desk, for example. The size of the analytic unit 202 may vary. A handheld unit in accordance with embodiments of the invention weighs less than two pounds.

Figure 8:
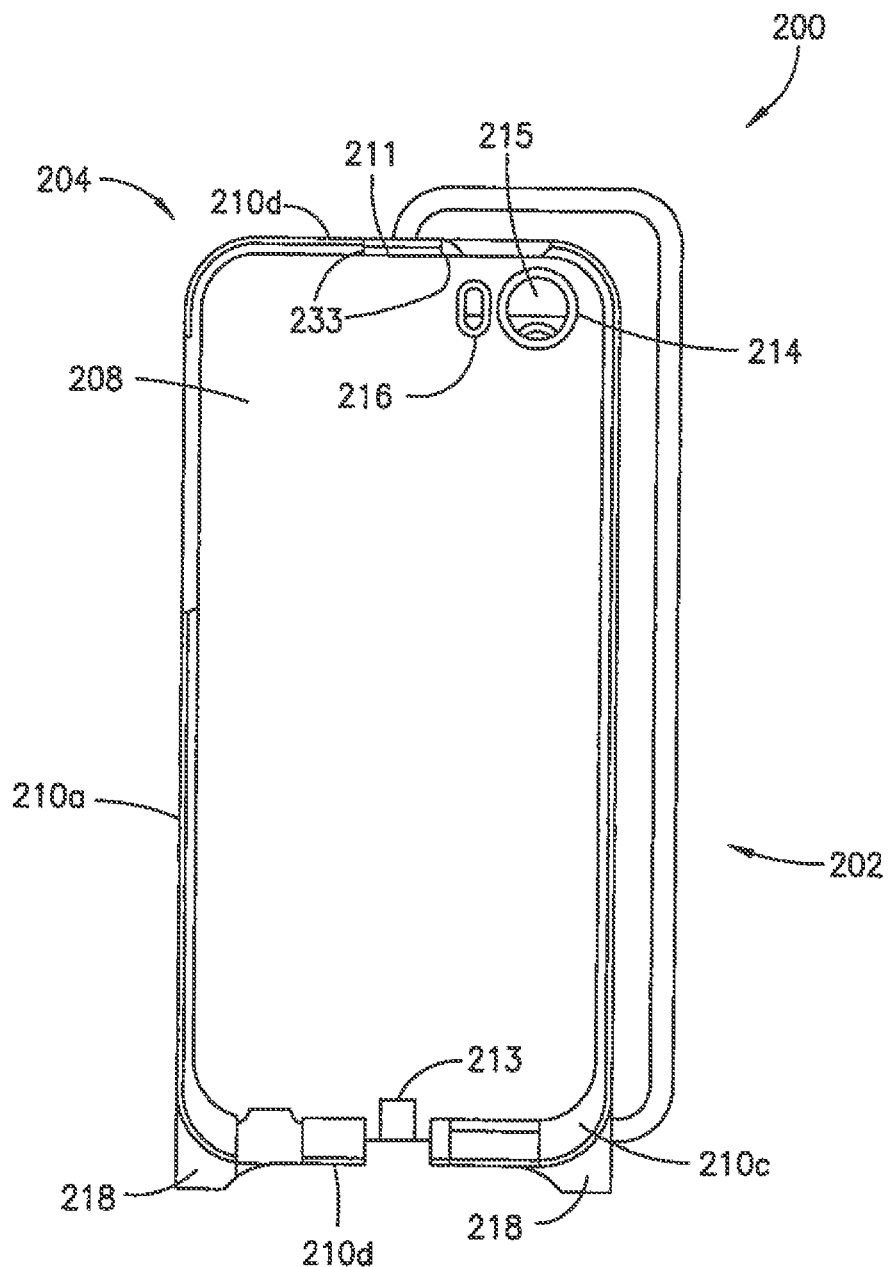

Returning to FIG. 6, the docking station 204 comprises a flat supporting plate 208 and a rim 210 extending from an edge 212 of the flat plate. The rim 210 may be configured to receive the smartphone 206 in a snapfit or a pressfit, for example. In this example, the smartphone 206 is retained in a snap-fit by flexible sections 210a-210d of the rim 210 that snap over the smartphone 206 when it is inserted into the docking station 204. An extended section 211 defined by slots 233 through the rim 210 extends from an edge of the rim, slightly over the smartphone 206, as shown in FIGS. 6-8 and 10, for example. The rim 210 comprises rim sections 210a-210d that extend partially around the edge 212 of the flat plate 208, to allow access to control buttons and ports on the edge of the smartphone 206, as shown in FIG. 8.

In a pressfit, the docking station 204 is configured so that the dimensions of the station, as defined by the location of the rim 210, is about the same as that of the smartphone 206 so that the rim bears against the sides of the smartphone when the smartphone is in the docking station. The docking station 204 may have other configurations, as well. For example, the docking station 204 may have a front face and the mobile electronic device 206 may be inserted into the docking station through a slot at the front or side of the station, for example. The front face of such a docking station 204 may be the front wall of the analytic unit 202 and the docking station can be interior to the analytic unit, for example.

FIG. 8 is a front view of the docking station 204. In this example, two holes 214, 216 are provided through the flat plate 208. One hole 214 is positioned to be aligned with the rear facing camera 52 of the smartphone 206. The second hole 216, which is optional, is aligned with the light source 53 to enable illumination by the flash of the smartphone 206, for calibration and for setting the ISO, the shutter speed, the white balance, and sensitivity settings of the camera 52. The second hole 216 is optional. The bottom of the docking station 204 may include extensions 218 to tilt the analytic device 200 when the device rests on a flat surface, such as a table or desk, for example, to facilitate use of the touchscreen on the smartphone 206.

An optical filter 215 may be provided in the first opening 214 (or a corresponding opening in the wall of the analytic unit 202) to limit passage of light below a predetermined wavelength, as discussed further below. The optical filter 215 acts as an emission filter that removes light emitted by the LED. For example, if the LED emits blue light, the filter removes blue light. In this way, the detected light will be the light emitted by the emission dye, not the light emitted by the LED. Examples of filters 15 that may be used include Wratten No. 15 gel filter that blocks wavelengths of 510 nm and below, or a Wratten No. 16 gel filter, that blocks wavelengths of 520 nm and below, (not shown) from The Eastman Kodak Co., Rochester, NY.

A connector 213 may be provided in the docking station 204 for the smartphone 206 to plug into, to provide direct electrical connection between the smartphone 206 and the analytic unit 202. A power supply port of an iPhone® may be connected to the connector 213 via a USB or other serial hardware connector, such as Apple® Lighting® connector, for example. The mobile electronic device may also communicate with the analytic device wirelessly, such as via Bluetooth wireless technology, for example.

Figure 9:
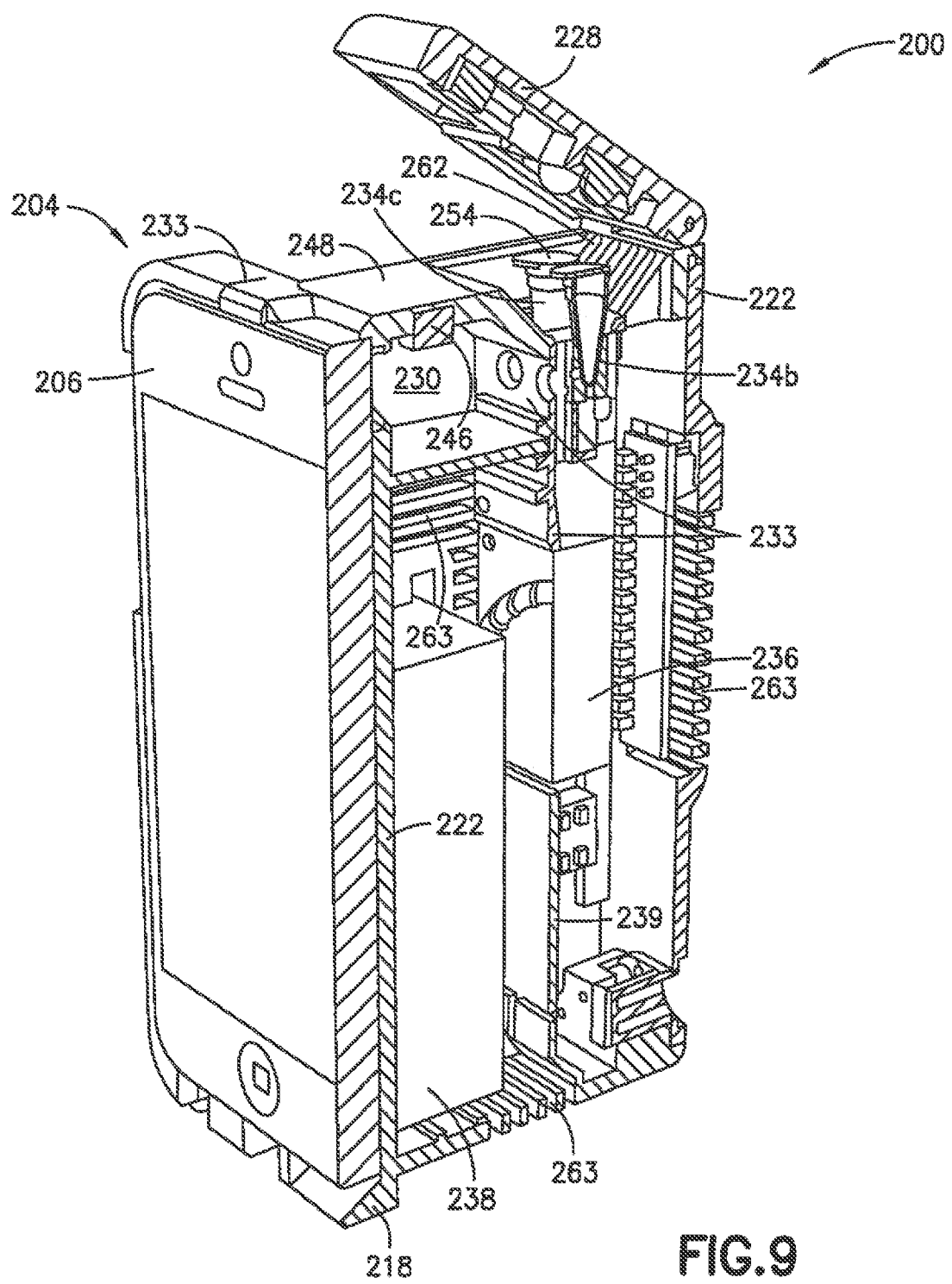

Returning to FIGS. 6 and 7, the analytic unit 202 comprises front and rear rectangular walls 220, 222, a first and second sidewalls 224, 226, and top and bottom, rectangular walls 228, 230, respectively. The top wall 228 is a hinged lid connected to the upper edge of the rear wall 222, enabling access to the upper portion of the interior of the analytic unit, (as shown in FIG. 9, for example). The first and second rectangular walls 224, 226 include semi-oval or semi-circular depressions 242 beneath edges of the lid 228, to facilitate opening of the lid by hand. Other shaped depressions may be provided. The walls of the analytic device 202 and the docking station 204 may be formed by a plastic or metal by any appropriate technique, such as by three-dimensional printing, forging, metal injection, welding, and/or casting with electrical discharge machining, for example.

The docking station 204 may be a separate component connected to the front rectangular wall 220 or the flat plate 208 may be formed integral with the front wall 220. When a separate component, the docking station 204 may be removably connected to the front wall 220 by a user by a sliding and/or snap mechanism, for example. This enables the user to connect a docking station 204 configured for different mobile electronic devices having different sizes.

Figure 10:
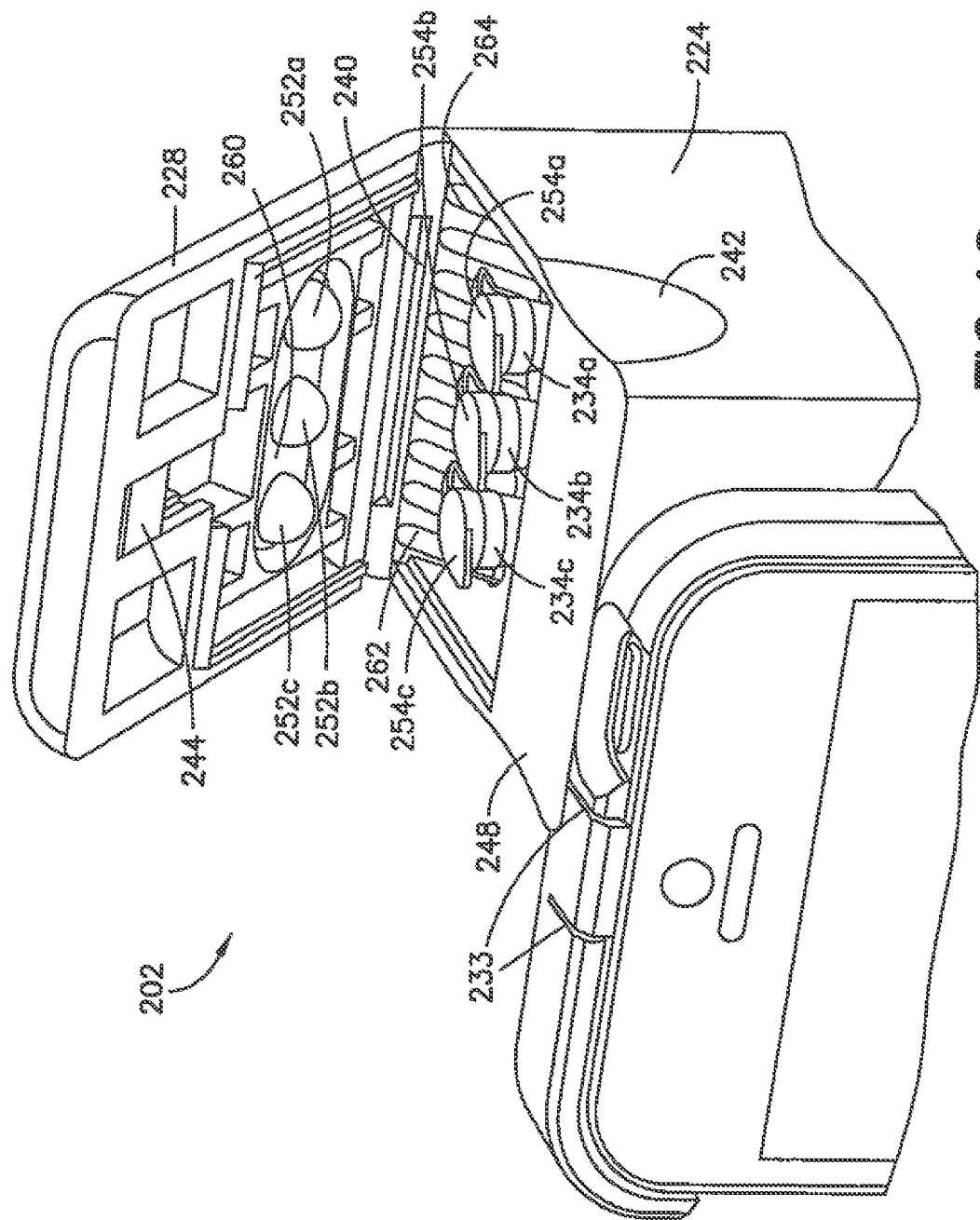

FIG. 9 is a perspective, partial cross-sectional, partial breakaway view of the PCR analytic device 200 of FIG. 7, with the smartphone 206 in the docking station 204, the first side wall 224 of the analytic device 202 removed, and the lid 228 in an open position. In an upper portion of the analytic device 202, a chamber 230 is provided between the front wall 220 and a plenum wall 233. In FIG. 9, a rear assay tube 234c is shown and a middle assay tube 234b is shown in cross-section. A front assay tube 234a is shown in FIG. 10 and other Figures. A blower or fan 236 is positioned below the assay tubes 232a, b, c. A battery 238 is positioned below the chamber 230. A battery charging circuit 239 is below the fan 236. The assay tubes 234c, 234b are in plenum behind the plenum wall 233, as discussed below.

FIG. 10 is an enlarged perspective view of the upper portion of the analytic unit 202 with the hinged lid 228 open, showing the tops of the three assay tubes 234a, 234b, 234c. More or fewer assay tubes 234 may be provided. The lid 228 in this example is connected to the rear rectangular wall 222 by a hinge 240. A magnet 244 is provided in a recess in the lid 228 and a magnet 246 (shown in FIG. 9) is provided in a recess in a ledge 248 to maintain the lid in a closed position. Other recesses in the lid 228 are provided to decrease the amount of material in the lid, decreasing the cost and weight of the analytic unit 200.

Figure 11:
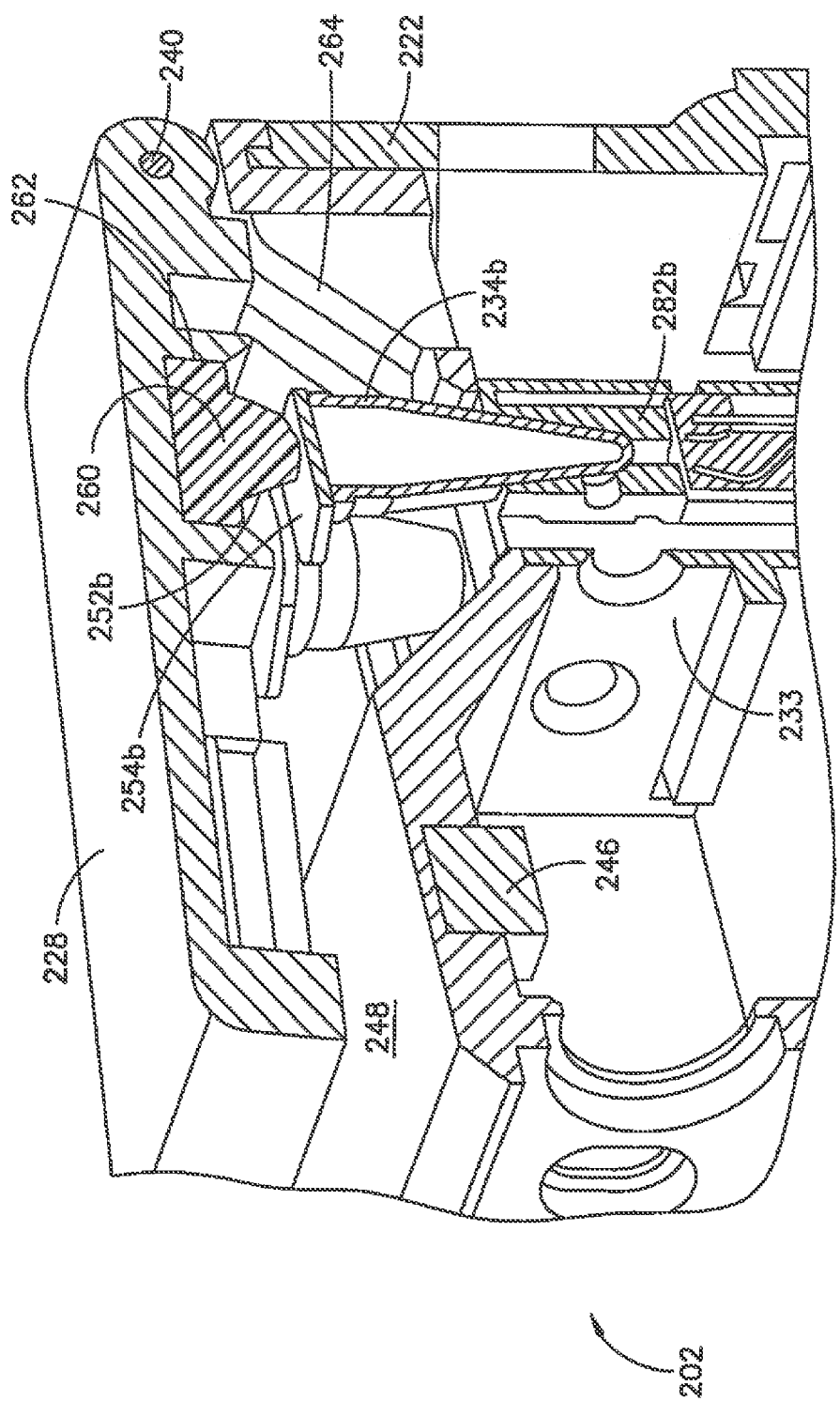
FIG. 11 is an enlarged perspective, partial breakaway, partial cross-sectional view of the upper portion of the analytic device of FIG. 9, with the lid closed.
Figure 13:
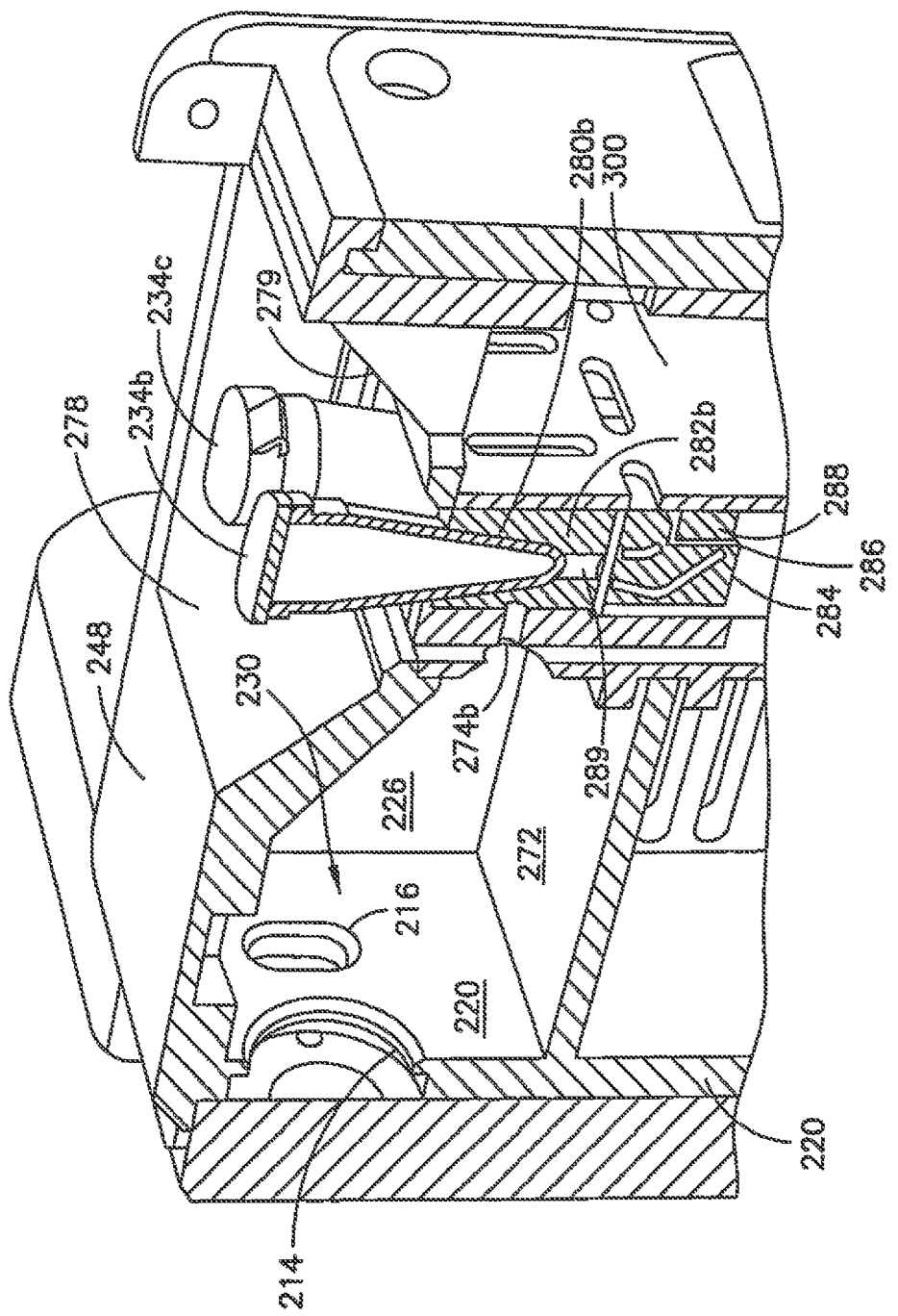
FIG. 13 is a rear perspective, partial breakaway, partial cross-sectional view of the upper portion of the analytic unit of FIG. 12, with the lid removed.

The interior surface of the lid 228 includes three protrusions 252a, 252b, 252c for bearing against the tops 254a, 254b, 254c of the three assay tube 234a, 234b, 234c, respectively. In FIG. 11, which shows the lid 228 in a closed position, the protrusion 252b bears against the top 254b of the assay tube 234b. In this example, the protrusions protrude from a common base 260. FIG. 13, which is a partial breakaway, partial cross-sectional view through the analytic unit 200 with the lid almost completely closed, shows the middle protrusion 252b in contact with the middle assay tube 234b. The middle protrusion 252b and the middle assay tube 234 are shown cross-section. The assay tubes in this example have a conical shape, and sit in respective conical recesses in respective heating blocks, as discussed further below.

The protrusion 252b in this example comprises the common base 260, which has a rectangular cross section, and the protruding section 252b, which has a semi-circular cross-section. The other protrusions 252a, 252c similarly protrude respective from the base 260. The base 260 is received within a rectangular recessed section in the lid. 262. The protrusions 252a, 252b, 252c provide a spring force against the assay tubes 234a, 234b, 234c, respectively, to improve their thermal contact with the surfaces of the recesses in the heating blocks 282. A spring force of from about 0.5 to about 4 pounds per square inch may be applied, for example. The protrusions 252a, b, c may comprise silicone rubber or other resilient elastomeric material, for example. Other configurations for providing a spring-like, bearing force against the assay tubes 234a, b, c may also be used such as coil or lead springs.

The tops 254a, 254b, 254c of the assay tubes 234a, 234b, 234c may be hinged caps that rotate about a hinge on the containers during opening and closing of the containers. The hinged caps in this example have edges with protrusions for engagement by a user's finger, to facilitate opening and closing of the lid 228. As noted above, any standard, off the shelf PCR tubes 234a, b, c may be used. For example, the assay tubes 234a, b, c may be 0.1 ml or 0.2 ml PCR tubes, or other thin-walled commercially available PCR tubes, for example. Suitable PCR tubes may be obtained from Phenix Research Products, Candler, North Carolina, for example.

FIGS. 10 and 11 show air exit vents 262 through the rear wall 222, behind the assay tubes 234a, b, c. The vents 262 in this example are defined by parallel walls 264 protruding from the rear wall 222 into the interior of the device 202, between the vents 262, as best shown in FIG. 10. Air inlet vents 263 are also provided in the side walls 224, 226 and bottom wall 230 to air to be drawn into the analytic device 202 by the fan 236 for cooling.

Figure 12:
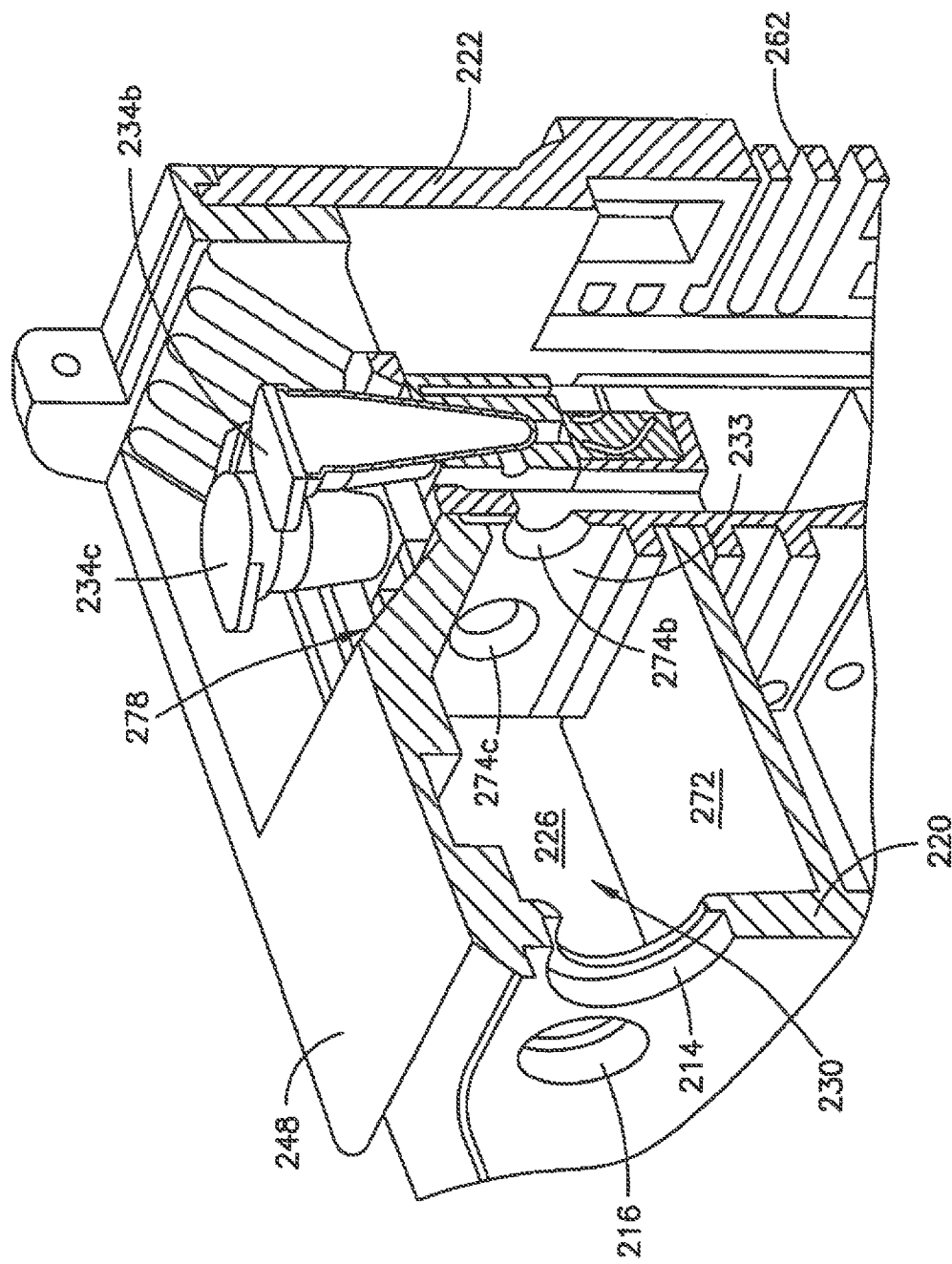
FIG. 12 is an upper perspective view of FIG. 11, with the lid removed.
Figure 14:
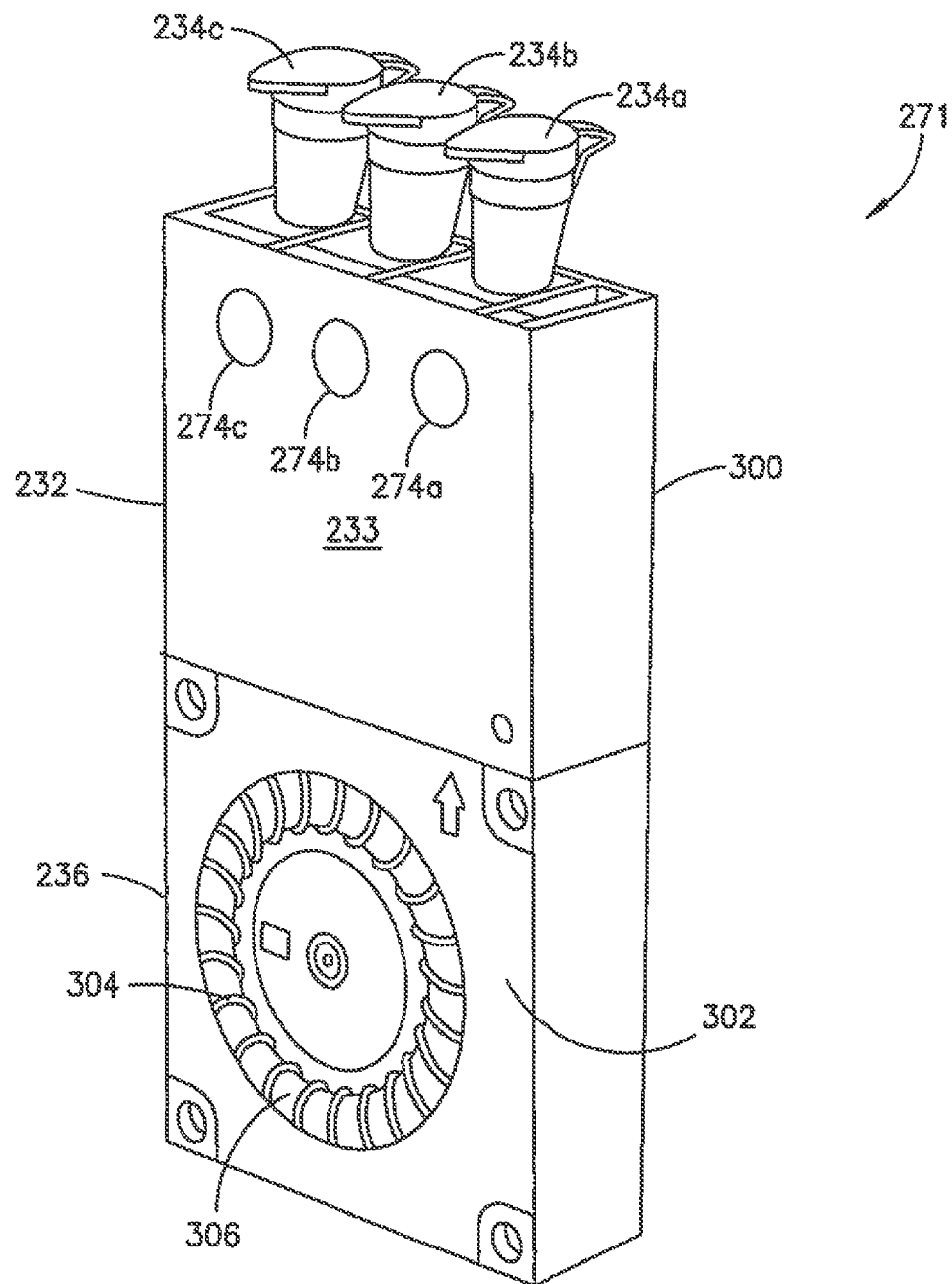
FIG. 14 is a perspective view of a core portion of the analytic unit.

FIG. 13 is a rear perspective, partial breakaway, partial cross-sectional view of the upper portion of the analytic unit 200, with the lid 228 removed. The chamber 230, shown in FIG. 11, is further defined by the second side wall 226 of the device, the first side wall 224 of the device (not shown in this view), and a bottom plate 272. The opening 216 and a portion of the opening 214 through the front plate 208 of the docking station, which also penetrate through the front wall 220 of the analytic unit 202, are shown. The plenum wall 233 defines three openings 274, as shown in FIG. 14. The rear opening 274c and a part of the middle opening 274b are shown in FIG. 12. The front opening 274a is not shown in this view. Each opening 274a, 274b, and 274b is positioned in front of an assay tube 234a, 234b, 234c, respectively, as shown in FIG. 14. In the view of FIG. 12, the openings 274c, 274b are shown in front of the assay tubes 234c, 234b. Inclined walls 278, 279 facilitate placement of the assay tubes 234a, b, c.

The assay tube 234b is received within a recess 280b defined in a heating block 282b. The chamber 230, which is one example is about 1.25 inches from the front wall 220 to the back wall 270, enables the field of view of the camera of the mobile electronic device 206 to encompass all of the assay tubes 234a, 234b, 234c. Below the heating block 282 is a light pipe 284. The light pipe 284 has an input surface 286 adjacent a light emitting diode ("LED") 288. An output side of the light pipe 284 is adjacent to an opening 289 defined in the heating block 282, below the recess 280. The heating block 282, the light pipe 284, and the LED 288 are mounted to a printed circuit board 300 as discussed further below.

FIG. 14 is a perspective view of a core portion 271 of the analytic device 202 and the fan 236 shown in FIG. 9, for example. The core has a rear wall that in this example is a printed circuit board 300. The plenum chamber wall 233 of the chamber 232 is part of core 271, in this example. As mentioned above, the assay tubes 234a, 234b, 234c, and the assay tube 234a, are supported between the printed circuit board 300 and the plenum wall 233. Openings 274a, 274b, 274c through the plate 233, which are shown in part in FIGS. 11 and 12, for example, are also shown.

The fan 236 in this example is also mounted to the printed circuit board 300. The fan 236 comprises a front wall 302 defining an intake 304. Fan blades 306 blow air upward in FIG. 14, through an open top of the fan, to a plenum chamber behind the intermediate wall 233, where the assay tubes 234a, b, c to cool the heating block 282 and other heating blocks described below. The fan 236 may be powered by a brushless DC motor, for example. The core 271 may be fastened to internal walls of the housing or supported by plastic bosses (not shown) in the walls, for example.

Figure 15:
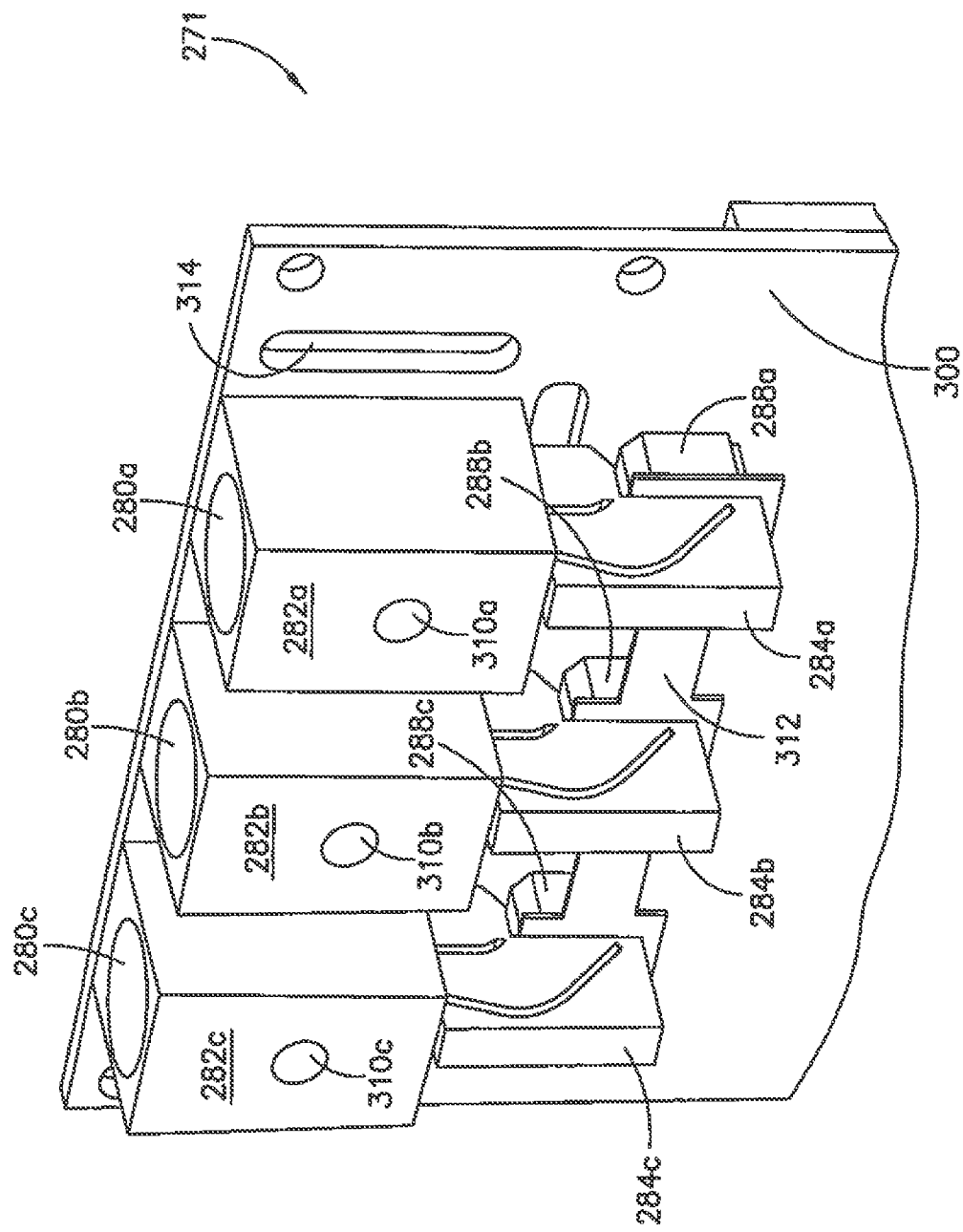
FIG. 15 is a perspective view of the upper portion of the core, with a plenum wall removed.

FIG. 15 is a perspective view of the upper portion of the core 271, with the plenum wall 233 removed. Three heating blocks 282a, 282b, 282c, each defining a recess 280a, 280b, 280c to receive a respective assay tube 234a, 234b, 234c (not shown in this view). Each heating block 282a, 282b, 282c also defines an opening 310a, 310b, 310c extending through each heating block to the respective recesses 280a, 280b, 280c. The openings 310a, 310b, 310c are aligned with the openings 274a, 274b, 274c, respectively, in the plenum wall 233 of FIG. 14, for example. The chamber 230, shown in FIG. 9, for example, has a sufficient length for the viewing angle of the rear facing camera 52 to encompass the three openings 274a, b, c, in order to image the three assay tubes 234a, b, c, through the openings 310a, b, c.

Three light pipes 284a, 284b, 284c are shown below each heating block 282a, 282b, 282c, respectively, as discussed above with respect to FIG. 15, for example. Three LEDs 288a, 288b, 288c are provided adjacent to input sides of the light pipes 284a, 284b, 284c, as was also discussed with respect to FIG. 15. The light pipes 284a, 284b, 284c guide the light received from the respective LEDs 288a, 288b, 288c by the input side of the light guide, to the output side of the respective light guide. In this example, the light provided by each LED 288a, 288b, 288c is reflected 90°. As shown in FIG. 13, for example, each heating block 282a, b, c also defines an opening 289 through the bottom of each heating tube to the bottom of the recess 280a, b, c for passage of the excitation light from each light pipe 282a, b, c to each assay tube 234a, b, c.

According to their specifications, LEDs 288a, b, c in one example emit blue light with a brightness of 550 mcd, a power of 130 mW, and a dominant wavelength of 470 nm, for example. The LEDs 288a, b, c may be obtained from Optic Technology, Inc., Pittsford, NY., for example. The light pipes 284a, 284b, 284c may comprise acrylic and may be formed by laser cutting, for example. One or more additional LEDs (not shown) may be provided adjacent each LED 288a, b, c to emit light at another wavelength, in order to excite different reporter dyes and test for additional types of nucleic acids. The assays may be excited at each wavelength in an alternating sequence or simultaneously.

An optical filter 312 is shown between the input sides of the LEDs 288a, 288b, 288c and the light pipes 284a, 284b, 284c. The optical filter 312 is an excitation filter configured to remove light emitted by the LEDs 288a, b, c having a wavelength that overlaps with the wavelength of assay dye emission. In this way, the light detected by the camera of the smartphone camera will not be from the LEDS. For example, the dye may be excited by blue light and emit green light. The optical filter 312 is therefore configured to filter green light in the light provided by the LEDs 288a, b, c. The optical filter 312 may be a Roscolux #385 Royal Blue lighting filter, available from Rosco Laboratories, Inc., Stanford, Connecticut, for example, which issued to comprise a co-extruded polycarbonate film having a thickness of 0.003 inches (76.2 microns). The filter 312 may be provided between the light pipes 284a, 284b, 284c instead. If additional LEDs are provided to provide excitation light at additional wavelengths, as discussed above, the optical filter 312 may comprise additional respective sections to appropriately filter the excitation light of the additional LEDs. The smartphone 206 may provide separate images resulting from excitation at each wavelength, or provide the captured data in a single images, for example.

A slot 314 through the printed circuit board 300 is also shown in FIG. 14 FIG. 15, which is a front view of FIG. 14, shows additional slots 314 adjacent to and between each heating block 282a, 282b, 282c. The slots 314 insulate the heating blocks 282*a*, *b*, *c* from each other, decreasing heat transfer from one block to an adjacent block, through the printed circuit board 300.

Figure 17:
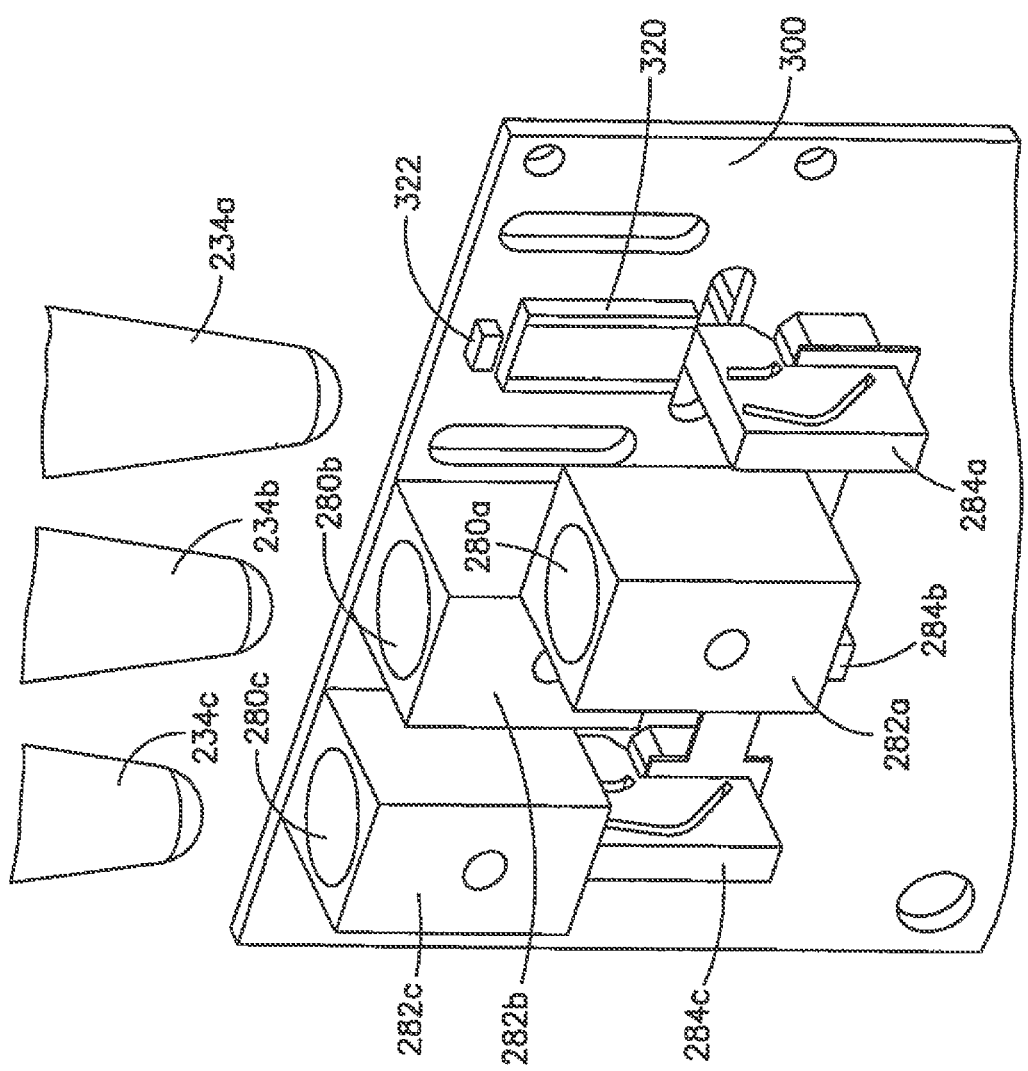
FIG. 17 is a similar view as the FIG. 15, with a heating block separated from the circuit board.
Figure 18:
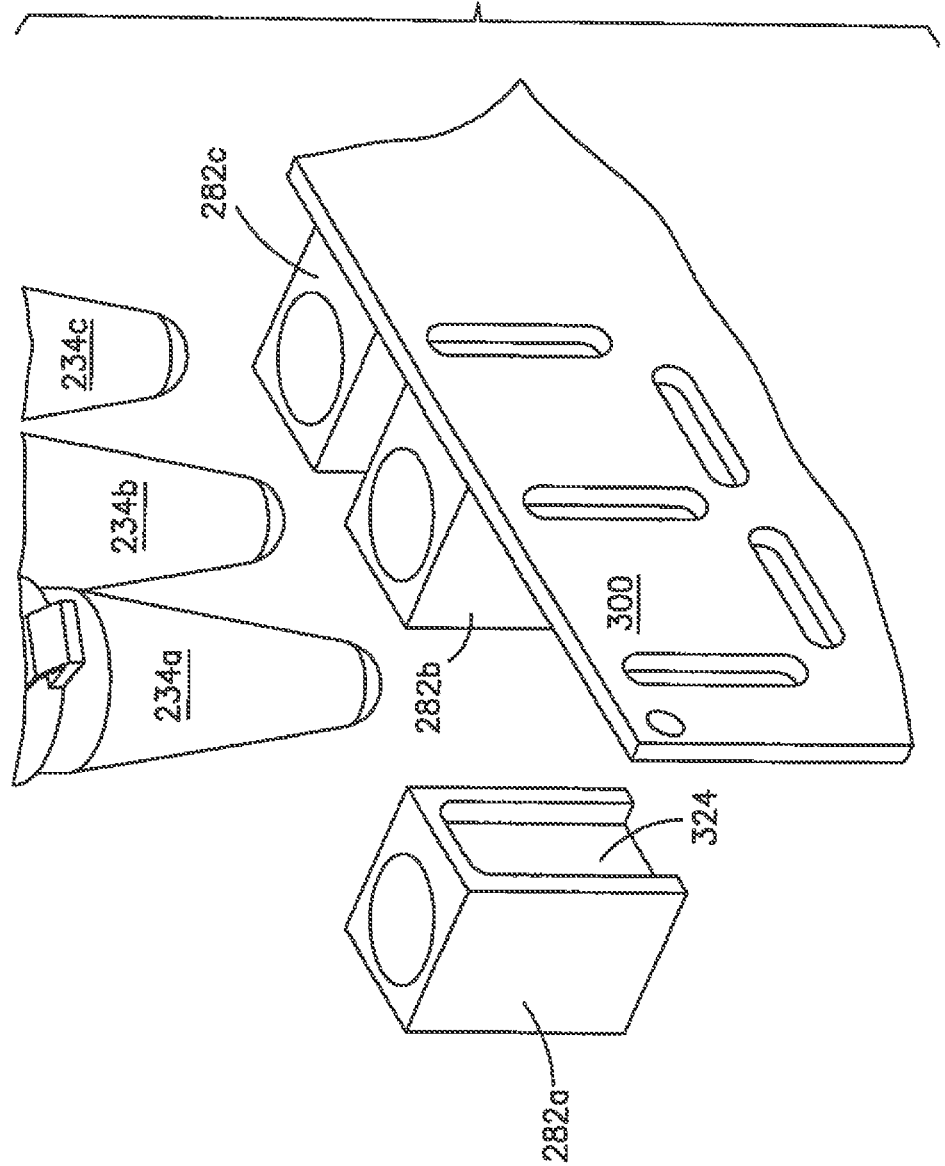
FIG. 18 is a rear perspective view of the core of FIG. 17.

FIG. 17 is similar to FIG. 15, except that the heating block 282*a* is shown separated from the printed circuit board 300, to show a resistive heater 320 mounted to the board. Respective resistive heaters and thermistors are mounted to the board 300 for the heating blocks 282*b* and 282*c*, as well. Also shown is a thermistor 322, which is also mounted to the board 300. The assay tubes 234*a*, *b*, *c*, are shown above the respective recesses 280*a*, *b*, *c*.

The resistive heater 320 may be a high chip SC3 Series power resister available from TT Electronics PLC, Surrey, England, for example. The SC3 series high chip power resistors are said to have a power dissipation at 70° C. of three watts, a resistance range of 1 RO to 10K, and an ambient temperature range of −55° C. to 150° C. The thermistor 322 may be a 10 kOhm NTC 0603 SMD thermistor available from Murata Electronics, North America, Smryma, Georgia, for example.

The processing device 330, the heating blocks 282*a*, *b*, *c*, the resistive heaters 320, the thermistor 322, and/or the LEDs 288*a*, *b*, *c* may be mounted to the circuit board 300 by a standard pick-and-place automation device conducting standard surface mount technology, in a manner known in the art. The same pick-and-place device may be used to mount all or several of these components, facilitating manufacture of and decreasing the cost of the board 300 and the analytic device 200.

Figure 16:
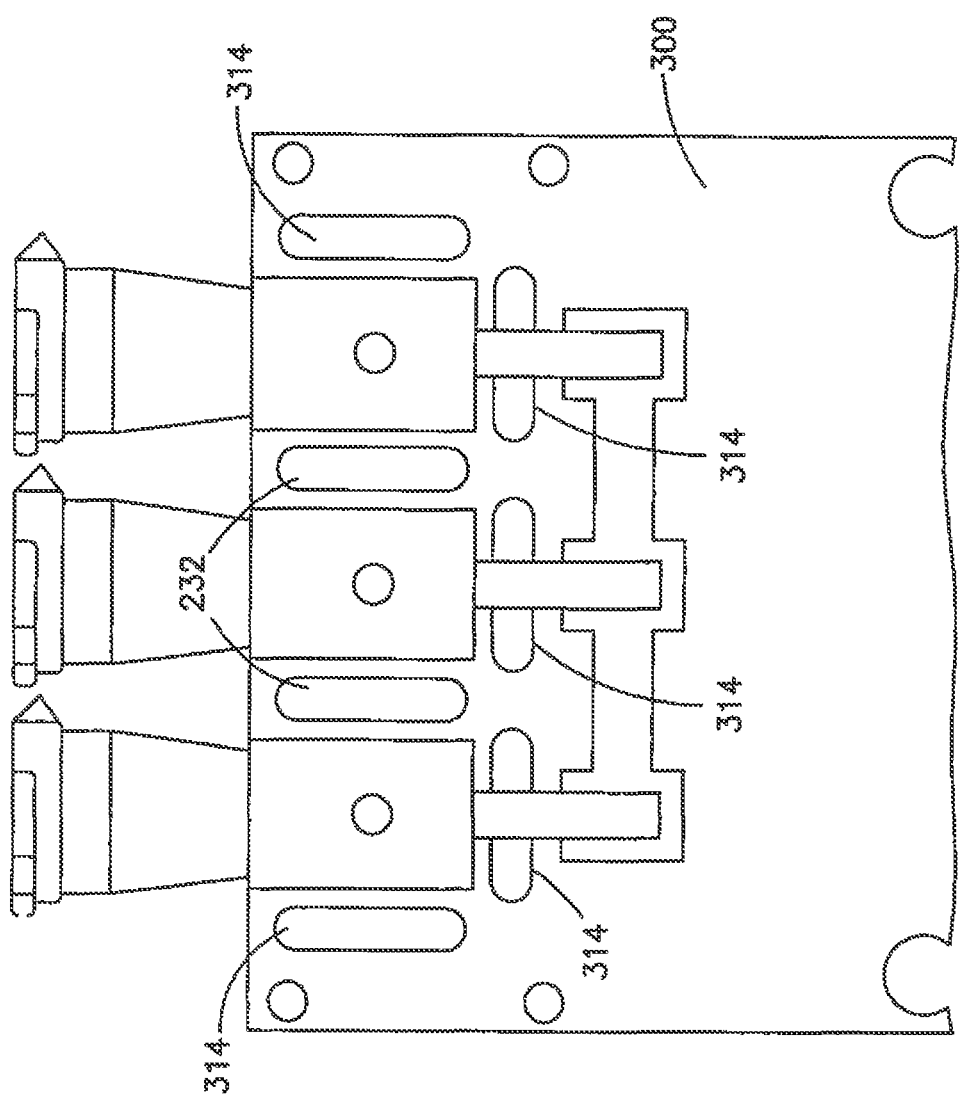
FIG. 16 is a front view of FIG. 15.

FIG. 17 is a rear perspective view of FIG. 16. The heating block 282*a*, as well as the heating blocks 282*b* and 282*c*, define a recess 324 configured to receive and encompass the resistive heater 320 and the thermistor 322 when the respective heating block is mounted to the printed circuit board 300. The heating blocks 282*a*, 282*b*, 282*c* may be surface mounted to the circuit board 300 and to the resistive heaters 320 and thermistors 322 by thermally conductive epoxy, for example, to provide intimate thermal contact. This results in accurate temperature readings and small thermal inertia.

By providing separate heating blocks 282*a*, *b*, *c* for each assay tube 234*a*, *b*, *c* in this embodiment, the mass of each heating block 382*a*, *b*, *c* is decreased, yielding blocks with a high surface area to volume ratio. This decreases the amount of time needed to heat the heating blocks 382*a*, *b*, *c* by the resistive heaters 320 and to cool the heating blocks by the fan 236 to desired temperatures to perform the assay procedure. More complex heating and cooling schemes are therefore not required. For best heating, the level of the assay in each assay tube 234*a*, *b*, *c* is no higher than the top of the respective heating block 382*a*, *b*, *c* when the assay tube is in a respective recess 280*a*, *b*, *c*.

The heating blocks 382*a*, 382*b*, 382*c* may be aluminum as aluminum alloy, such as 6061 which is readily available. The heating blocks 382*a*, *b*, *c* may be formed by machining, for example.

The heating blocks 282*a*, *b*, *c* have a volume at least as large as the volume of the fluid to be heated in the assay tubes. In one example, the volume of fluid in each assay tube 234*a*, *b*, *c* is from about 5 to about 100 microliters, for example. The dimensions of each heating block 282*a*, 282*b*, 282*c* may be about 0.25 inches×0.18 inches×0.25 inches, for example.

Figure 19:
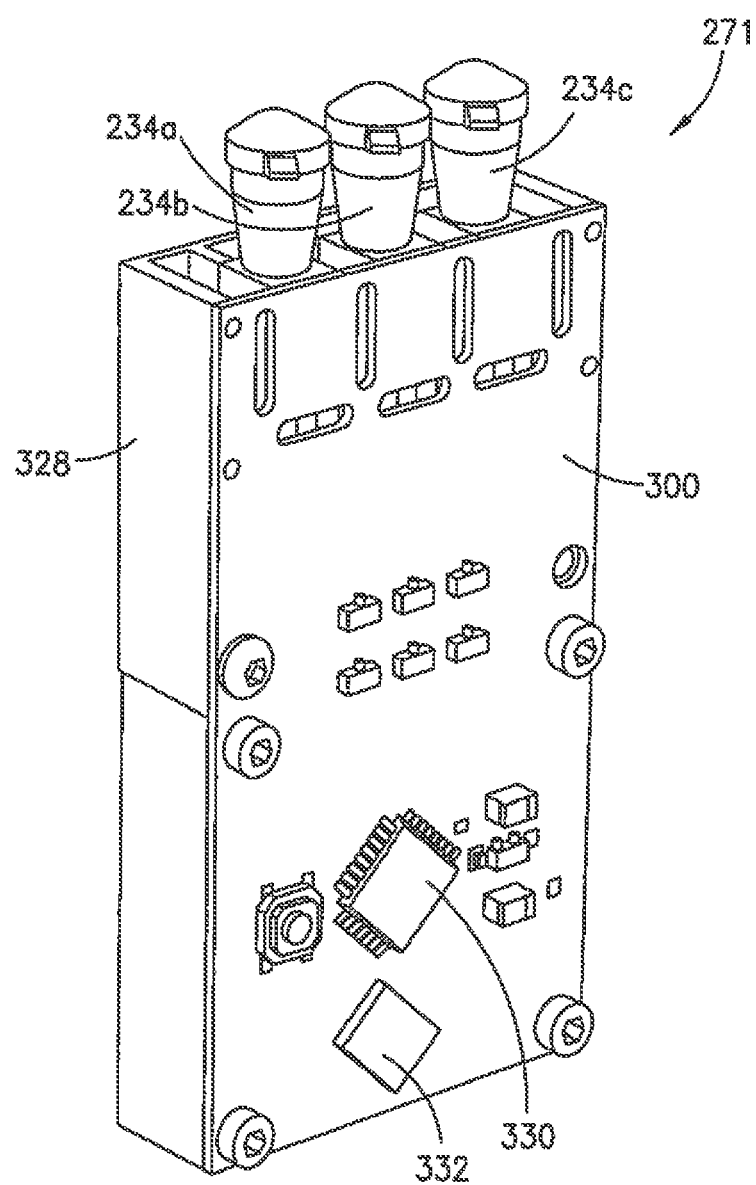
FIG. 19 a rear perspective view of the upper portion of the core of FIG. 15.

FIG. 19 is a rear view of the core 271 showing the printed circuit board 300, the assay tubes 234*a*, *b*, *c*, and the fan 236. A side wall 328, in conjunction with an opposite side wall not shown in this view, guides the air from the fan toward the heating blocks 384*a*, *b*, *c*. The rear side of the board 300 includes a processing device, such as a microprocessor or a microcontroller for example. In this example, the processing device 330 is a microcontroller. The microcontroller is electrically coupled to and controls the operation of the resistive heaters 320, the fan 236, and the LEDs 288*a*, *b*, *c*. The microcontroller 330 is also electrically coupled to the thermistors 322 to monitor the temperatures of the respective heating blocks. The microcontroller 330 also communicates with the smartphone 206 to receive instructions concerning the assay procedure and to provide information concerning the procedure to the smartphone wirelessly (via Bluetooth in this example). The microcontroller 330 may also communicate via direct electrical connection, as discussed above.

Operation of the processing device 330 is controlled by software stored in memory in the analytic unit, which may be part of the processing device and/or be mounted to the circuit board 300. The processing device 330 of the smartphone 206 provides inputs to the processing device 330, such as temperatures, and instructions, such as turning on and off the resistive heaters, as described below. The microcontroller may be an ATmega 32U4 central processing unit, from Atmel, Corporation, San Jose, California, on an Arduino electronics platform, for example. A separate surface mountable wireless communication chip 332 enabling wireless communication between the processing device 330 and the mobile electronic device 206, may also be surface mounted to the circuit board 300. The wireless communication chip may be a Bluetooth® chip, such as a Bluetooth® Low Energy System-on-Chip, TI CC2540, from Texas Instruments, Dallas, Texas.

In another example, the resistive heaters 320 are mounted to the opposite side of the circuit board 300 than the heating blocks 282*a*, *b*, *c*. In this case, the resistive heaters 320 may be thermally coupled to the heating blocks 282*a*, *b*, *c* by standard plated through hole vias in the circuit board 300, as is known in the art.

The battery 238, which powers the analytic unit 202, may be a rechargeable battery, for example. A lithium ion or lithium polymer battery may be used, for example. The analytic unit 202 may include a port to receive a charger plug to recharge the battery by wall power, for example. The PCR device 202 may also be powered by an external source of power, such as standard wall power, via a wall transformer/adaptor or other such UL listed device to provide low DC voltage.

An example of a PCR procedure performed by the analytic device 200 will be described with respect to a test for *Neisseria gonorrhoeae*. The temperatures and time periods in this example may vary for different target nucleic acid sequences, and for particular analytic devices. A urine sample is obtained and processed, if required, prior to DNA isolation, in a manner known in the art. The DNA may be isolated in accordance with the Boom method or other method known in the art by the user conducting the test or another party, for example. The user of the analytic device 200 inserts the isolated DNA solution into an assay tube 234*a* containing lyophilized reagents specific to *Neisseria gonorrhoeae* from a PCR test kit. The assay tube 234*a* is shaken and the lyophilized reagents dissolve in the solution. The user opens the lid 228 and inserts the assay tube 234*a* into a recess 280*a* in a heating block 282*a*, for example. A pure water sample is introduced into another assay tube, such as tube 234*b*, for example, to serve as a non-template control, and inserted into the heating block 282*b*, for example. A positive control solution is inserted into another assay tube, such as the tube 234*c*, and inserted into the heating block 282c, for example. As noted above, the pure water sample should show no fluorescence, unless there is contamination, and the positive control solution should fluoresce if the analytic unit 202 performs the PCR procedure correctly, under the control of the smartphone 206. For best heating, the level of the assay in each assay tube 234a, b, c is no higher than the top of the respective heating block 382a, b, c when the assay tube is in a respective recess 280a, b, c.

The user may then insert (or has previously inserted) a camera enabled mobile electronic device 206, such as a smartphone, into the docking station 204. The user opens a PCR App on the smartphone 206 and selects the appropriate gonorrhea test protocol. A start button is displayed on the display 18 and the user may touch the button to start the test.

Wireless or direct electrical connection between the smartphone 206 and the processing device 330 of the analytic device 202 is confirmed by the smartphone 206 and the process temperatures are provided by the smartphone 206 to the processing device, which stores the temperatures in memory. For this PCR procedure, four temperatures T1, T2, T3, T4 are provided, where T1=100.0 degrees C., T2=95.0 degrees C., T3=57.5 degrees C., and T4 equals 60.0 degrees C.

Under the control of the smartphone 206, the analytic unit 202 causes the heating blocks 234a, b, c to heat to T1 (100.0 degrees C.) by turning on the resistive heaters 320. This starts the initial denaturing phase of the PCR procedure, where DNA strands in this example are separated to form single strands. When all the heating blocks 234a, b, c reach the temperature T1, as determined by each thermistor 322, the temperature is held for a first predetermined Time Period 1 of 6.5 seconds.

At the end of the first predetermined Time Period 1, the resistive heaters 320 are turned off under the control of the smartphone 206, allowing the heating blocks 234a, b, c to cool to the second temperature T2 of 95 degrees C. The temperature T2 is held for two minutes, continuing the denaturing process.

At the end of second predetermined time period T2 of two minutes, the analytic unit 202 cools the heating blocks 234a, b, c to the temperature T3 of 57.5 degrees C., by turning on the fan 236. When the temperature T3 is reached, the fan 236 is turned off and the heating blocks 234a, b, c are held for a second predetermined Time Period 3 of three seconds, under the control of the smartphone 206, to start the annealing phase of the PCR procedure.

After three seconds, the resistive heaters 320 are turned on to heat the heating blocks 232a, b, c to the fourth temperature T4 of 60.0 degrees C. When the fourth temperature T4 is reached, the resistive heaters 320 are turned off and the heating blocks 234a, b, c are held at T4 for a fourth predetermined Time Period 4, to start the annealing phase of the PCR procedure. During annealing, the primers attach to a complementary sequence and polymerase joins the dNPT to the 3' prime end of the primer, forming a complementary sequence. Annealing continues during the fourth predetermined Time Period 4 of 20 seconds.

Image capture by the rear facing camera 52 of the smartphone 206 takes place during the fourth predetermined Time Period 4, after the start of the Time Period 4. In this example, image capture begins 15 seconds after the beginning of the fourth Time Period 4 and proceeds for five seconds, until the end of the fourth Time Period 4. Image capture may be in a video mode or in a single image mode.

Luminosity data, for example, is derived from the captured images by applying image processing techniques known in the art by the processing device of the smartphone 206, under the control of the PCR App, for example. In one example, the luminosity values of the images captured in each cycle may be averaged. The luminosity data may be expressed in the form of a graph that shows the luminosity values from each cycle, over the entire PCR procedure, as is known in the art. The presence of a target nucleic acid sequence and the initial concentration of the target nucleic acid sequence may be determined from the graph, by the PCR App and/or by the user. The graph may be displayed on the display screen 18 of the smartphone, and/or sent to a third party via a network, for analysis and storage, for example. In another example, the PCR App provides an output that the target nucleic acid sequence is present or not.

The process then returns to the first denaturing step at the first temperature T1 and the process is repeated over multiple cycles, such as for 40 cycles or for a user defined number of cycles, for example. In this example, the only difference between the first cycle and the subsequent cycles is that the second Time Period 2 at 95 degrees C. is only held for one second.

FIGS. 20-26 show a flowchart 500 of an example of the operation of the smartphone 206 and the analytic unit 202 in accordance with an embodiment of the invention, based on the gonorrhea PCR procedure described above. The actions of the smartphone 206 or other mobile electronic device is described in the left column, and the actions of the PCR analytic unit 202 are shown in the right column. The flowchart is applicable to the PCR analytic unit 10 of the first embodiment, as well.

Figure 20:
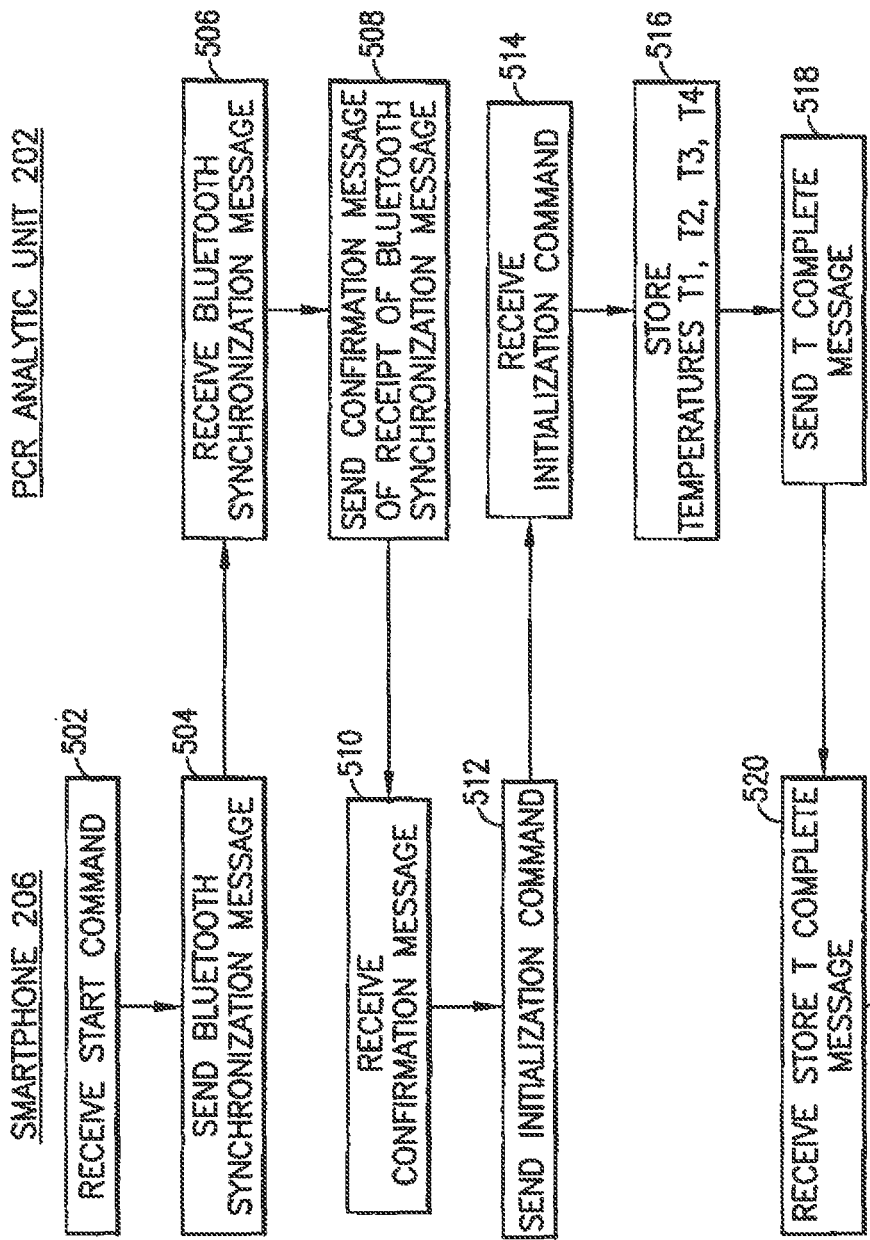
FIGS. 20-26 are a flowchart of an example of the operation of the PCR analytic device of FIGS. 6-19.

A start command is received by the smartphone 206, in Step 502 in FIG. 20. The start command may be entered by PCR App stored on the smartphone 206, when or after the PCR App is opened, for example. In response to the start command, in this example the smartphone 504 sends a Bluetooth synchronization message to the PCR analytic device 202, in Step 504, to confirm that there is a Bluetooth connection between the smartphone 206 and the analytic unit 202. If the smartphone 206 and the PCR analytic unit 202 are connected via an electrical connection port, the connection and proper communication can be confirmed by other methods known in the art. The Bluetooth synchronization message may comprise one or more messages, such as a heartbeat type message, that needs to be confirmed within predetermined periods of time, for example. For example, the analytic unit 202 may need to respond to the synchronization message within 10 seconds. If the Bluetooth synchronization message is received in Step 506, the unit 202 sends a message confirming receipt, in Step 508. It is noted that this confirmation procedure may be performed continuously throughout the PCR procedure. If at any time a confirmation message is not received, the assay procedure is aborted.

If the smartphone 206 receives the confirmation message with the predetermined time, in Step 510, the processing device of the smartphone, under the control of the PCR App, for example, sends an initialization command, in Step 512. In this example, the initialization command includes four target temperatures T1, T2, T3, T4 to be used in the PCR process to be performed by the unit 202. The temperatures T1-T4, as well as the predetermined Time Periods, in the method 500 are the same as the temperatures and time periods discussed above in the PCR procedure to determine whether *Neisseria gonorrhoeae* is present. In other PCR assay procedures, more or fewer temperatures, and different temperatures, may be used.

The analytic unit 202 receives the initialization command in Step 514 and the processing device 330 stores the temperatures T1-T4 in memory, in Step 516. When temperatures T1-T4 are stored, the processing device 330 sends a message to the smartphone 206 that storage of the temperatures is complete, in Step 518. The smartphone 202 receives the store temperature complete message in Step 520.

Figure 21:
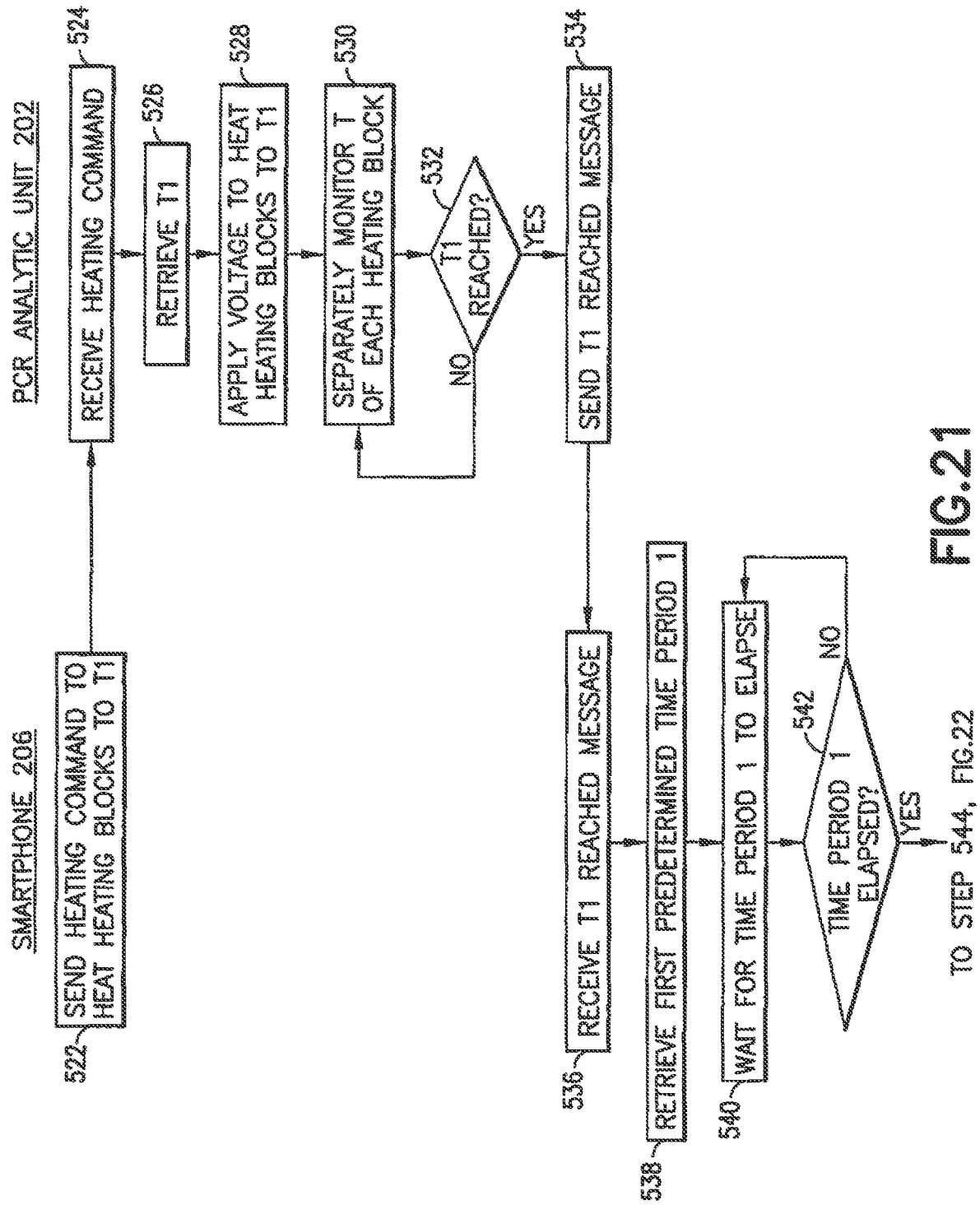
Figure 22:
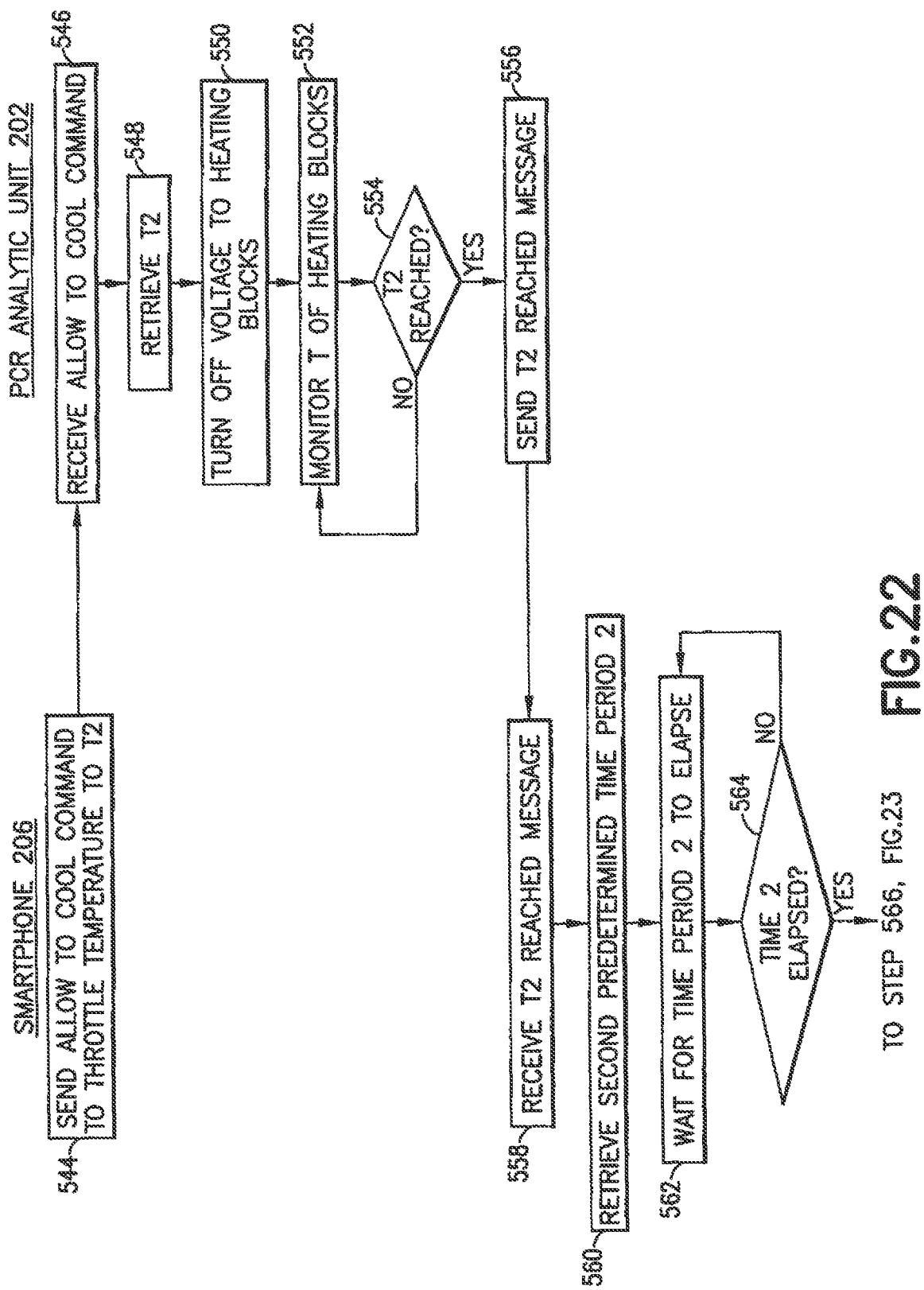

When the store temperature complete message is received by the smartphone 206, the method 500 continues in FIG. 21 at Step 522, where the processing device of the smartphone 206, under the control of the PCR App, sends a heating command to the analytic unit 202. The heating command instructs the unit 202 to heat the heating blocks 282a, b, c, in this example to the temperature T1.

The processing device 330 of the unit 202 receives the heating command in Step 524 and retrieves the temperature T1 from memory in Step 526. The processing device 330 then applies a voltage to the resistive heaters 320 so that they heat the heating blocks 282a, b, c, in Step 528.

The processing device 330 then monitors the temperatures of the heating blocks 282a, b, c via the thermistors 322, in Step 530. The processing device 330 checks whether T1 is reached, within tolerances, in Step 532. The processing device 330 may check by comparing the current temperature with the retrieved temperature T1. In this example, tolerances for the temperatures T1-T4 may be from about 0.25 degrees centigrade to about 0.50 centigrade may be acceptable, for example. If T1 is not reached, then the processing device 330 continues to monitor the temperature in Step 530 and check the temperature in Step 532. The processing device 330 waits until all of the heating blocks 282a, b, c reach the temperature T1. If T1, and the other temperatures discussed, in this example, for each heating block, are not reached within a predetermined period or periods of time, then an error message may be provided to the smartphone 206. The smartphone 206 can indicate the error to the user via the display 18 and/or the speaker 22, for example. Error detection is not indicated in the flowchart 500, but could be readily implemented by one of ordinary skill in the art. When T1 is reached, the processing device 330 sends a T1 reached message to the smartphone 206, in Step 534.

The smartphone 206 receives the T1 reached message in Step 536. The processing device of the smartphone 206 then retrieves a first predetermined Time 1 from memory, in Step 538. The processing device waits for the predetermined Time Period 1 to elapse, in Step 540. The processing device checks whether the predetermined Time Period 1 has elapsed, in Step 542. The processing device may check whether the Time Period 1 has elapsed by counting down from the predetermined Time Period 1 to zero, based on an internal clock, and checking whether zero is reached, in Step 542, for example. If not, the processing device returns to Step 540 and checks again in Step 542. If it is determined in Step 540 that the Time Period 1 has elapsed, the processing device proceeds to Step 544, in FIG. 22.

In Step 544, the processing device sends a command to the unit 202 to allow the heating blocks 282a, b, c to cool to the temperature T2. The allow to cool message is received by the unit 202, in Step 546. In response, the processing device 330 of the unit 202 retrieves the temperature T2 from memory, in Step 548, and turns off the voltage to the resistive heaters 320, in Step 550. The processing device 330 monitors the temperatures of the heating blocks 282a, b, c, in Step 552, and determines whether the temperature T2 is reached, in Step 554. This may be determined as discussed above with respect to Steps 530, 532. If the temperature T2 is not reached, the processing device continues to monitor the temperature of the heating blocks 282a, b, c, in Step 552, and determine whether the temperature is reached, in Step 554.

If the temperature T2 is reached, the processing device 330 sends a T2 reached message to the smartphone 206, in Step 556. When the smartphone 206 receives the T2 reached message, in Step 558, the processing device of the smartphone retrieves the second predetermined Time Period 2. The processing device waits for the Time 2 to elapse in Steps 562, 564, as discussed above with respect to Steps 540, 542.

Figure 23:
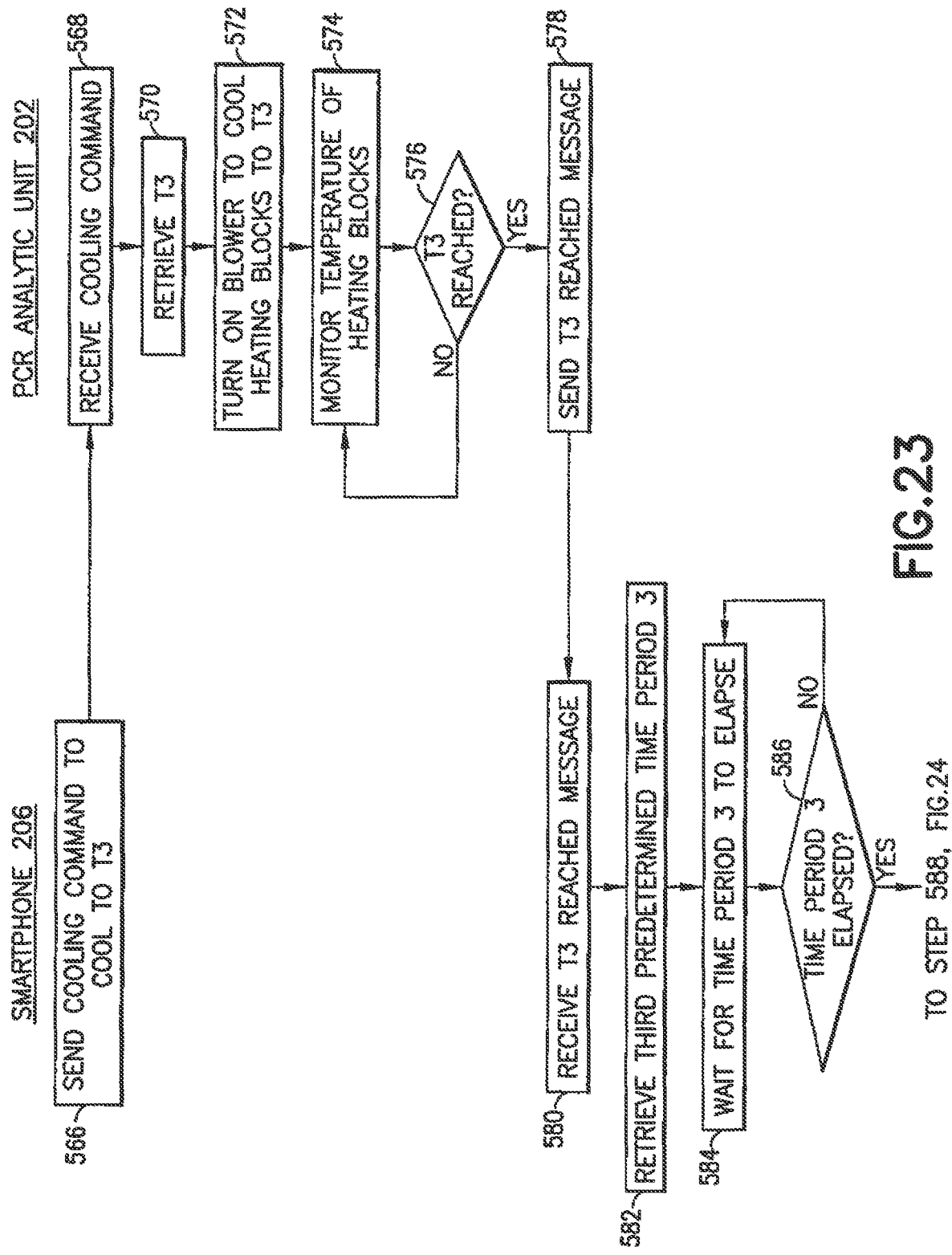

When the processing device of the smartphone 206 determines that the Time 2 has elapsed, the method 500 proceeds to Step 566 in FIG. 23, where the processing device of the smartphone 206 sends to the analytic unit 202 a command to cool the heating blocks to temperature T3. The unit 202 receives the cooling command in Step 568, and the processing device 330 retrieves the temperature T3 from memory in Step 570. The processing device 330 turns on the blower to cool the heating blocks 282a, b, c, in Step 572.

The processing device 330 then monitors the temperatures of the heating blocks 282a, b, c, in Steps 574 and 576 in the same manner as discussed above with respect to Steps 552 and 554. When the temperature T3 is reached, the processing device sends a T3 reached message to the smartphone 206 in Step 578.

The smartphone 206 receives the T3 reached message, in Step 580, and the processing device retrieves the third predetermined Time Period 3 from memory, in Step 582. The processing device then waits for the Time Period 3 to elapse, in Steps 584 and 586, as described with respect to Steps 540 and 542.

Figure 24:
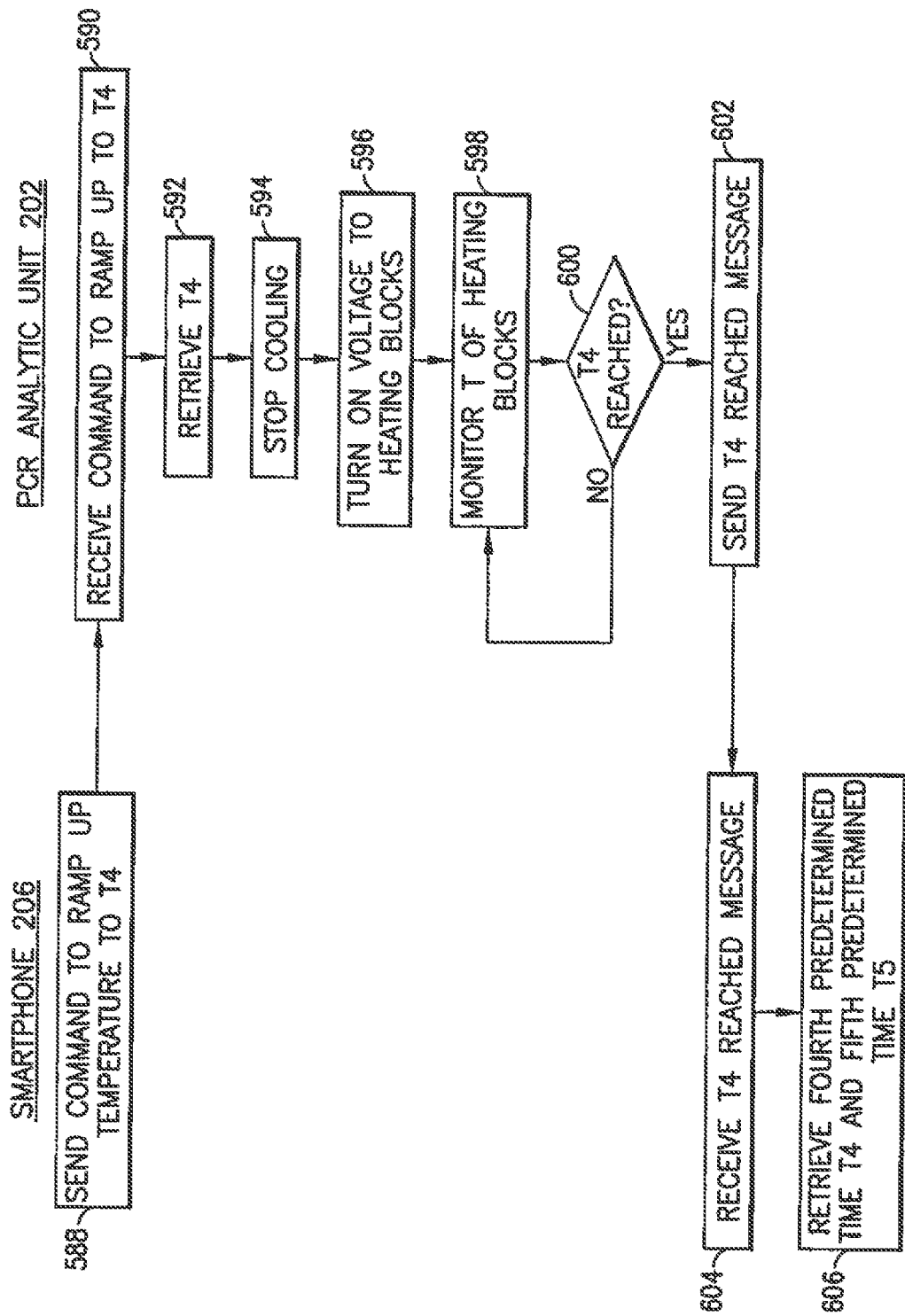
Figure 25:
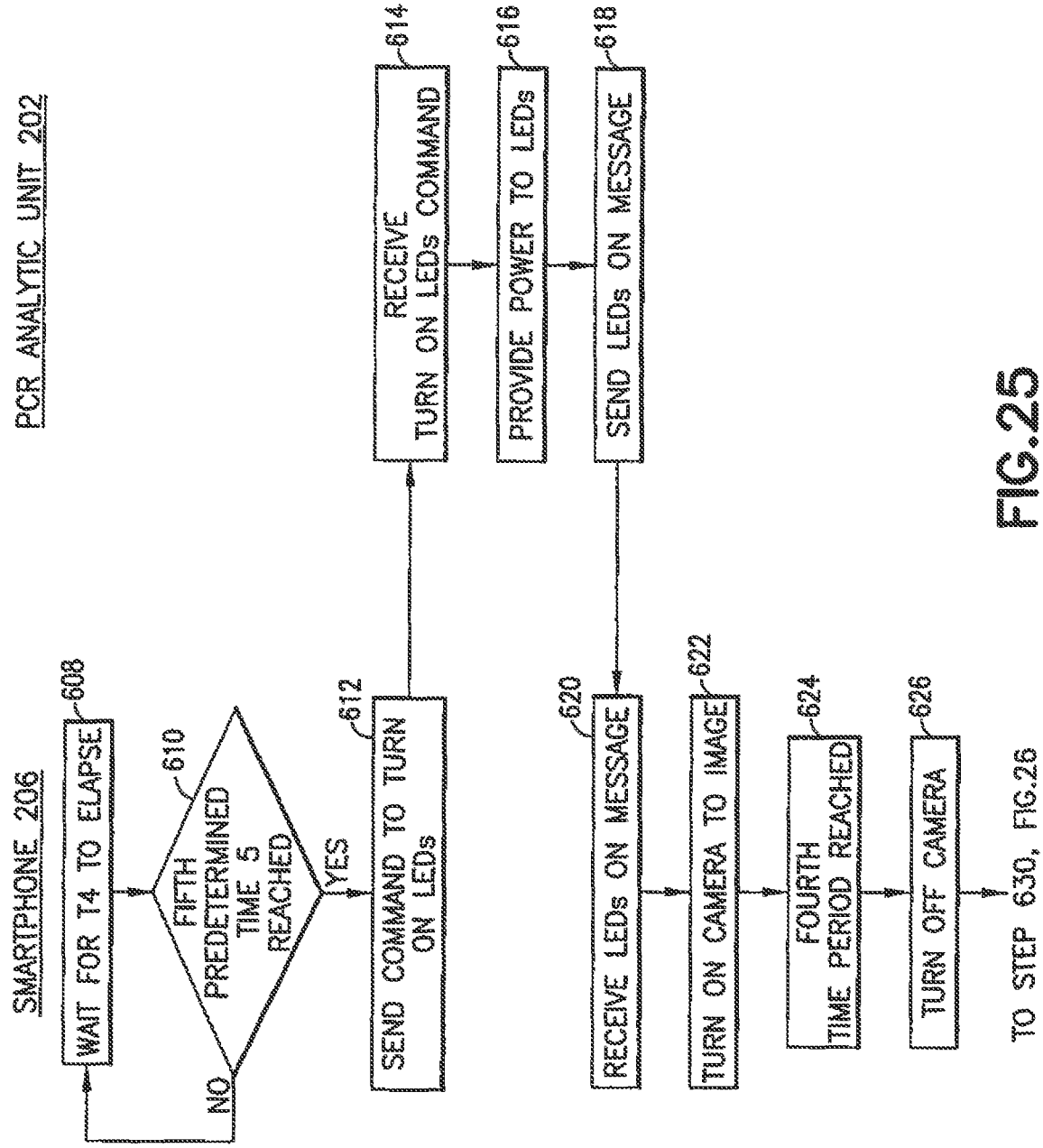

When the Time Period 3 has elapsed, the method 500 proceeds to Step 588 in FIG. 24, where the processing device of the smartphone 206 sends a command to the unit 202 to ramp the temperature of the heating blocks to the temperature T4. The ramp command is received by the processing device 330 of the unit 202, in Step 590. The processing device 330 retrieves T4 from memory, in Step 592, stops the cooling in Step 594 by turning off the blower, in Step 594, and starts heating the heating blocks 282a, b, c in Step 596 by turning on the voltage to the resistive heaters 320. The processing device 330 then monitors the temperature of the heating blocks 282a, b, c via the thermistors 322, in Steps 598 and 600, as discussed above with respect to Steps 552 and 554. When the temperature T4 is reached, the processing unit 330 sends a T4 reached message to the smartphone 206 in Step 602.

The smartphone 206 receives the T4 reached message, in Step 604, and the processing device retrieves the fourth predetermined Time Period 4, and the fifth predetermined Time 5 after the start of the fourth Time Period T4, in Step 606. The processing device of the smartphone 206 then waits for the Time 4 to elapse, in Step 608 in FIG. 25.

While waiting for the Time Period 4 to elapse, the processing device checks whether a fifth predetermined Time T5 is reached in Step 610. The processing device may do this by counting from the start of the fourth predetermined Time Period T4 to the Time T5.

When the Time Period T5 is reached, imaging starts. The processing device sends a message to the unit 202 to turn on the LEDs, in Step 612. The unit 202 receives the message, in Step 614 and the processing device 330 provides power to the LEDs 288a, b, c, in Step 616.

An LEDs on message is then sent to the smartphone 206, in Step 618. The message is received by the smartphone 206 in Step 620, and the processing device of the smartphone turns on the rear facing camera 52, in Step 622. The camera 52 is on until the end of the fourth Time Period T4 is reached. The camera 52 may take a video of the assay, or a series of individual images.

Figure 26:
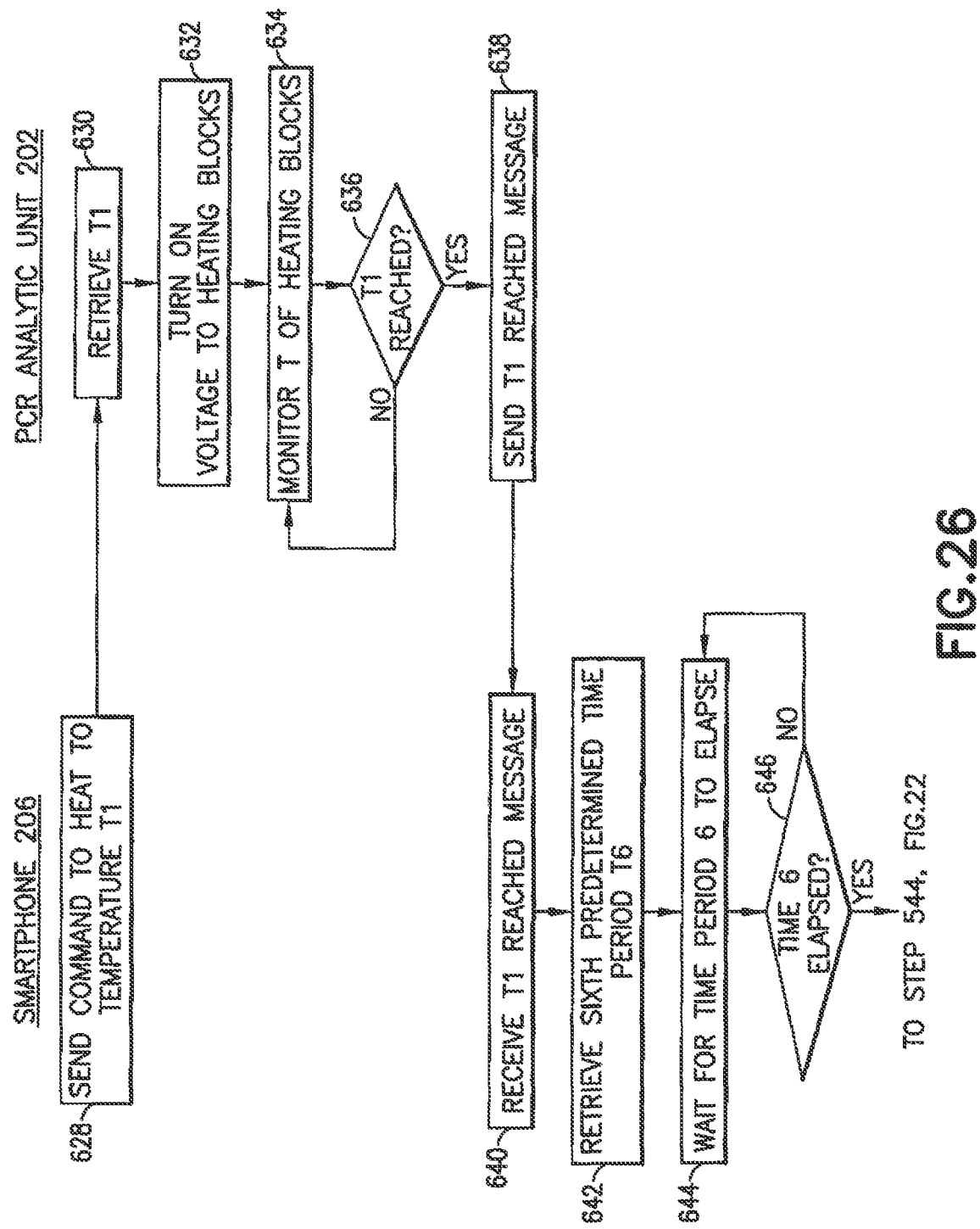

When the fourth Time Period T4 is reached in Step 624, the processing device turns off the camera 52, in Step 626, and proceeds to Step 630 in FIG. 26.

The smartphone 206 sends a command to the analytic unit 202 to heat the heating blocks to 282*a, b, c* to the first temperature T1, to start a new thermal cycle. In this and subsequent cycles, the first temperature T1 is held for a Time Period 6 different from the first Time Period 1, as discussed above.

The processing device 330 of the analytic unit 202 retrieves the temperature T1 in Step 630, turns on the voltages to the resistive heaters 320 in Step 632, and monitors the temperatures of the heating blocks 382*a, b, c*, via the thermistors 322 in Step 634. When the temperature T1 is reached, in Step 636, the processing device sends a T1 reached message to the smartphone 206, in Step 638.

The smartphone 206 receives the T1 reached message in Step 640, and the processing device of the smartphone retrieves a sixth predetermined Time Period 6, in Step 642, and waits for the Time Period 6 to elapse, in Step 644. When the Time Period 6 elapses, the method 500 proceeds to Step 544 in FIG. 22, to continue the second and subsequent thermal cycles and image capture.

Examples of implementations of embodiments of the invention are described above. Modifications may be made to those examples without departing from the spirit and scope of the invention, which is defined in the claims, below.

The invention claimed is:

1. A portable analytic device for processing a sample, comprising:
   a container comprising said sample;
   a holder configured to secure said container;
   a heater configured to heat said sample in said container;
   a mobile electronic device;
   a processor comprising a circuit operatively coupled to said heater, wherein said processor is configured to:
   (a) receive one or more instructions from said mobile electronic device for processing said sample, and
   (b) in response to said one or more instructions, use said one or more instructions to direct said heater to heat said sample; and
   an opening in said heater configured for imaging of said processing.

2. The portable analytic device of claim 1, wherein said holder comprises a heating block, and wherein said heater is in thermal communication with said heating block.

3. The portable analytic device of claim 2, wherein said heating block comprises a recess configured to secure said container.

4. The portable analytic device of claim 2, wherein said heating block comprises a plurality of heating blocks and said heater comprises a plurality of heating units, and wherein a given heating block of said plurality of heating blocks is in thermal communication with a given heating unit of said plurality of heating units.

5. The portable analytic device of claim 2, wherein said heating block comprises a plurality of fins.

6. The portable analytic device of claim 2, wherein said heater comprises a resistive heater, and wherein said heater is thermally cured to said heating block.

7. The portable analytic device of claim 2, wherein said heater is at least partially disposed within an additional recess in said heating block.

8. The portable analytic device of claim 2, further comprising a cooling unit operatively coupled to said processor, wherein said processor is configured to implement temperature cycling of said sample within said container via said heating block and said cooling unit based, at least in part, on said one or more instructions from said mobile electronic device.

9. The portable analytic device of claim 1, wherein said one or more instructions comprise a temperature of said heater and/or a duration that said heater is held at said temperature.

10. The portable analytic device of claim 1, further comprising a communication unit that is configured to provide wireless communication between said processor and said mobile electronic device.

11. The portable analytic device of claim 1, further comprising a data exchange unit that is configured to communicate with said mobile electronic device, wherein said data exchange unit is configured to (i) receive said one or more instructions from said mobile electronic device, or (ii) provide results to said mobile electronic device upon processing said sample.

12. The portable analytic device of claim 1, further comprising an excitation source positioned to expose said sample to an excitation energy.

13. The portable analytic device of claim 1, wherein said mobile electronic device comprises a detector to detect a signal from said container to generate data, which data is presented on said mobile electronic device.

14. The portable analytic device of claim 1, wherein said sample is a biological sample.

15. The portable analytic device of claim 1, wherein said sample comprises a nucleic acid molecule.

16. The portable analytic device of claim 15, wherein said processing comprises amplifying said nucleic acid molecule.

17. The portable analytic device of claim 16, wherein amplifying said nucleic acid molecule comprises performing a polymerase chain reaction (PCR) procedure.

18. The portable analytic device of claim 1, wherein said mobile electronic device comprises a CMOS sensor.

19. The portable analytic device of claim 1, wherein said heater comprises a hot air heater.

20. The portable analytic device of claim 2, further comprising a temperature sensor configured to detect the temperature of said heating block.

* * * * *